United States Patent
Gross et al.

(10) Patent No.: US 10,758,722 B2
(45) Date of Patent: Sep. 1, 2020

(54) ELECTRICAL TREATMENT OF PARKINSON'S DISEASE

(71) Applicant: RAINBOW MEDICAL LTD., Herzliya (IL)

(72) Inventors: Yossi Gross, Moshav Mazor (IL); Alex Tendler, Haifa (IL); Gideon Fostick, Givat Shmuel (IL)

(73) Assignee: RAINBOW MEDICAL LTD., Herzliya (IL)

( * ) Notice: Subject to any disclaimer, the term of this patent is extended or adjusted under 35 U.S.C. 154(b) by 142 days.

(21) Appl. No.: 15/969,411

(22) Filed: May 2, 2018

(65) Prior Publication Data

US 2018/0318575 A1 Nov. 8, 2018

Related U.S. Application Data

(60) Provisional application No. 62/500,747, filed on May 3, 2017.

(51) Int. Cl.
*A61N 1/05* (2006.01)
*A61N 1/08* (2006.01)
*A61N 1/20* (2006.01)

(52) U.S. Cl.
CPC ......... *A61N 1/0536* (2013.01); *A61N 1/0534* (2013.01); *A61N 1/08* (2013.01); *A61N 1/205* (2013.01)

(58) Field of Classification Search
None
See application file for complete search history.

(56) References Cited

U.S. PATENT DOCUMENTS

| | | |
|---|---|---|
| 4,044,774 A | 8/1977 | Corbin et al. |
| 4,503,863 A | 3/1985 | Katims |
| 5,088,977 A | 2/1992 | Sibalis |
| 5,121,754 A | 6/1992 | Mullett |
| 5,433,739 A | 7/1995 | Sluijter et al. |
| 5,529,574 A | 6/1996 | Frackelton |

(Continued)

FOREIGN PATENT DOCUMENTS

| | | |
|---|---|---|
| WO | 94/05369 | 3/1994 |
| WO | 01/52931 | 7/2001 |

(Continued)

OTHER PUBLICATIONS

Karran Sep. E et201 al., 1 "The Amyloid cascade hypothesis for AD," Nature Reviews Drug Discovery, vol. 10; 698-712.

(Continued)

*Primary Examiner* — Brian T Gedeon
(74) *Attorney, Agent, or Firm* — Sughrue Mion, PLLC

(57) ABSTRACT

Apparatus is provided that includes a parenchymal electrode, configured to be implanted in brain parenchyma of a subject identified as at risk of or suffering from a synucleinopathy; and a cerebrospinal fluid (CSF) electrode, configured to be implanted in a CSF-filled space of a brain of the subject, the CSF-filled space selected from the group consisting of: a ventricular system and a subarachnoid space. Control circuitry is configured to drive the parenchymal and the CSF electrodes to clear alpha-synuclein (aSyn) from the brain parenchyma into the CSF-filled space of the brain. Other embodiments are also described.

28 Claims, 11 Drawing Sheets

(56) References Cited

U.S. PATENT DOCUMENTS

| | | |
|---|---|---|
| 5,792,100 A | 8/1998 | Shantha |
| 5,911,223 A | 6/1999 | Weaver et al. |
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,941,172 B2 | 9/2005 | Nachum |
| 6,997,941 B2 | 2/2006 | Sharkey et al. |
| 7,013,177 B1 | 3/2006 | Whitehurst et al. |
| 7,120,489 B2 | 10/2006 | Shalev et al. |
| 7,217,351 B2 | 5/2007 | Krumme |
| 7,223,227 B2 | 5/2007 | Pflueger |
| 7,270,659 B2 | 9/2007 | Ricart et al. |
| 7,317,947 B2 | 1/2008 | Wahlstrand et al. |
| 7,398,121 B2 | 7/2008 | Matsumura et al. |
| 7,509,171 B2 | 3/2009 | DiMauro |
| 7,640,062 B2 | 12/2009 | Shalev |
| 7,818,063 B2 | 10/2010 | Wallace et al. |
| 7,831,306 B2 | 11/2010 | Finch et al. |
| 7,860,569 B2 | 12/2010 | Solberg et al. |
| 8,060,207 B2 | 11/2011 | Wallace et al. |
| 8,190,248 B2 | 5/2012 | Besio et al. |
| 8,353,853 B1 | 1/2013 | Kyle et al. |
| 8,457,761 B2 | 6/2013 | Wariar |
| 8,577,469 B2 | 11/2013 | Gross |
| 8,676,348 B2 | 3/2014 | Gross |
| 8,731,674 B2 | 5/2014 | Wallace et al. |
| 9,616,221 B2 | 4/2017 | Gross |
| 9,724,513 B2 | 8/2017 | Lane et al. |
| 9,724,515 B2 | 8/2017 | Fostick et al. |
| 9,731,122 B2 | 8/2017 | Gross |
| 10,398,884 B2 * | 9/2019 | Lad .................. A61M 25/0026 |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0116977 A1 | 6/2004 | Finch et al. |
| 2004/0210209 A1 | 10/2004 | Yeung et al. |
| 2005/0010205 A1 | 1/2005 | Hovda et al. |
| 2005/0021104 A1 | 1/2005 | DiLorenzo |
| 2005/0119650 A1 | 6/2005 | Sanders et al. |
| 2005/0137646 A1 | 6/2005 | Wallace et al. |
| 2005/0137647 A1 | 6/2005 | Wallace et al. |
| 2005/0159790 A1 | 7/2005 | Shalev |
| 2005/0187589 A1 | 8/2005 | Wallace et al. |
| 2005/0203599 A1 | 9/2005 | Garabedian et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0162086 A1 | 7/2007 | DiLorenzo |
| 2007/0213700 A1 | 9/2007 | Davison et al. |
| 2007/0255338 A1 | 11/2007 | Wahlstrand |
| 2008/0009927 A1 | 1/2008 | Vilims |
| 2008/0119907 A1 | 5/2008 | Stahmann |
| 2008/0260542 A1 | 10/2008 | Nishikawa et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0312816 A1 | 12/2009 | Gross |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0054518 A1 | 3/2011 | Carbunaru et al. |
| 2011/0160638 A1 | 6/2011 | Mauge et al. |
| 2011/0160797 A1 | 6/2011 | Makous et al. |
| 2012/0053659 A1 | 3/2012 | Molnar et al. |
| 2012/0203307 A1 | 8/2012 | Schroeppel et al. |
| 2013/0066392 A1 | 3/2013 | Simon et al. |
| 2013/0102952 A1 * | 4/2013 | Gross .................. A61N 1/205 604/20 |
| 2013/0166006 A1 | 6/2013 | Williams |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 * | 10/2014 | Gross .................. A61N 1/327 607/62 |
| 2015/0011927 A1 | 1/2015 | Hua |
| 2015/0119898 A1 | 4/2015 | Desalles et al. |
| 2016/0331970 A1 | 11/2016 | Lozano |
| 2017/0007823 A1 | 1/2017 | Gross |
| 2017/0056642 A1 | 3/2017 | Moffitt et al. |
| 2017/0120053 A1 | 5/2017 | Fostick et al. |
| 2017/0182317 A1 | 6/2017 | Gross et al. |
| 2017/0296821 A1 | 10/2017 | Fostick et al. |
| 2018/0071523 A1 | 3/2018 | Gross et al. |
| 2018/0193646 A1 | 7/2018 | Fostick et al. |

FOREIGN PATENT DOCUMENTS

| | | |
|---|---|---|
| WO | 01/85027 | 11/2001 |
| WO | 2001/085094 | 11/2001 |
| WO | 2006/090397 | 8/2006 |
| WO | 2008/007369 | 1/2008 |
| WO | 2017/006327 | 1/2017 |
| WO | 2017/072769 | 5/2017 |
| WO | 2017/115351 | 7/2017 |
| WO | 2018/051338 | 3/2018 |

OTHER PUBLICATIONS

De La Tone JC, "Vascular Basis of Alzheimer's Pathogensis," Ann NY Acad Sci. 977:196-215 (Nov. 2002).

Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.

Brief PubMed search for metal ions in Alzheimers.

An Office Action dated Sep. 27, 2016, which issued during the prosecution of U.S. Appl. No. 14/926,705.

An International Search Report and a Written Opinion both dated Aug. 7, 2008, which issued during the prosecution of Applicant's PCT/IL2007/000865.

An Office Action dated Mar. 29, 2013, which issued during the prosecution of U.S. Appl. No. 12/373,306.

An Office Action dated Oct. 31, 2011, which issued during the prosecution of U.S. Appl. No. 12/373,306.

An Office Action dated Oct. 1, 2012, which issued during the prosecution of U.S. Appl. No. 12/373,306.

Notice of Allowance dated Jul. 24, 2013, which issued during the prosecution of U.S. Appl. No. 12/373,306.

An Office Action dated Apr. 11, 2013, which issued during the prosecution of U.S. Appl. No. 13/663,757.

Notice of Allowance dated Oct 28, 2013, which issued during the prosecution of U.S. Appl. No. 13/663,757.

Elixmann IM et al., "In-vitro evaluation of a drainage catheter with integrated bioimpedance electrodes to determine ventricular size," Biomed Tech 2013; 58 (Suppl. 1) Sep. 2013 (2 pages total).

An Office Action dated Aug. 31, 2015, which issued during the prosecution of U.S. Appl. No. 13/872,794.

An Applicant Initiated Interview Summary dated Dec. 14, 2015, which issued during the prosecution of U.S. Appl. No. 13/872,794.

(56) References Cited

OTHER PUBLICATIONS

An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017, which issued during the prosecution of Applicant's PCT/IL2016/051161.
Notice of Allowance dated Jul. 14, 2017, which issued during the prosecution of U.S. Appl. No. 13/872,794.
An Office Action dated May 26, 2017, which issued during the prosecution of U.S. Appl. No. 15/453,290.
An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP—Renal Physiol Aug. 1, 1997 vol. 273 No. 2 F307-F314.
U.S. Appl. No. 60/830,717, filed Jul. 12, 2006.
Dao-Sheng Liu et al., "Activation of Na+ and K+ Pumping Modes of (Na,K)-ATPase by an Oscillating Electric Field," The Journal of Biological Chemistry, vol. 265. No. 13, May 5, 1990. (pp. 7260-7267).
Robert F. Service . . . "Electric fields deliver drugs into tumors." http://news.sciencemaa.ora. Feb. 4, 2015. (5 Pages Total).
Vernengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits," Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.
An International Search Report and a Written Opinion both dated Mar. 10, 2017, which issued during the prosecution of Applicant's PCT/IL2016/051363.
An Office Action dated Apr. 25, 2018, which issued during the prosecution of U.S. Appl. No. 15/637,330.
U.S. Appl. No. 62/444,939, filed Jan. 11, 2017.
Borlase NM, "The thalamus in Parkinson's Disease," Department of Psychology, University of Canterbury, 2012.
Fernandes J, "Protein May Prevent Neuron Death in Huntington's Patients, Study Finds," huntingtonsdiseasenews.com, Jan. 19, 2017.
Lee H-J, "Extracellular αsynuclein a novel and crucial factor in Lewy body diseases," Nat. Rev. Neurol. 10, 92-98 (Feb. 2014); published online Jan. 28, 2014.
Starr PA et al., "Parkinson's Disease FAQ—Deep Brain Stimulation for Parkinson's Disease," UCSF Apr. 19, 2017.
Perez RG et al., "A Role for Alpha-Synuclein in the Regulation of Dopamine Biosynthesis," The Journal of Neuroscience, Apr. 15, 2002, 22(8):3090-3099.
Breydo L et al., "α-Synuclein misfolding and Parkinson's disease," Biochimica et Biophysica Acta 1822 (2012) 261-285 (Available online Oct. 12, 2011).
Deleidi M et al., "Protein Clearance Mechanisms of Alpha-Synuclein and Amyloid-Beta in Lewy Body Disorders," International Journal of Alzheimer's Disease, vol. 2012.
Xie L et al., "Sleep Drives Metabolite Clearance from the Adult Brain," Science. Oct. 18, 2013; 342(6156).
Valdinocci D et al., "Potential Modes of Intercellular α-Synuclein Transmission," International Journal of Molecular Sciences, Feb. 22, 2017.
U.S. Appl. No. 62/500,747, filed May 3, 2017.
Sawyer, P N et al. "Measurement of streaming potentials of mammalian blood vessels, aorta and vena cava, in vivo." Biophysical journal vol. 6,5 (1966): 641-51. doi:10.1016/S0006-3495(66)86683-3, https://www.ncbi.nlm.nih.gov/pmc/articles/PMC1368020/, viewed on Jul. 22, 2019.
An Office Action dated Jul. 29, 2019, which issued during the prosecution of U.S. Appl. No. 15/618,325.
An Office Action dated Jul. 10, 2019, which issued during the prosecution of U.S. Appl. No. 15/864,065.
An International Search Report and a Written Opinion both dated May 23, 2019, which issued during the prosecution of Applicant's PCT/IL2019/050284.
An Office Action dated Mar. 25, 2019, which issued during the prosecution of U.S. Appl. No. 15/742,245.
An Office Action dated Jan. 7, 2020, which issued during the prosecution of U.S. Appl. No. 15/618,325.

\* cited by examiner

ELECTRICAL TREATMENT OF PARKINSON'S DISEASE

CROSS-REFERENCE TO RELATED APPLICATIONS

The present application claims the benefit of U.S. Provisional Application 62/500,747, filed May 3, 2017, which is assigned to the assignee of the present application and is incorporated herein by reference.

FIELD OF THE APPLICATION

The present invention relates generally to treatment and prevention of Parkinson's disease, and specifically to electrical techniques for treating, preventing, or slowing the progression of Parkinson's disease.

BACKGROUND OF THE APPLICATION

Parkinson's disease (PD) is a long-term degenerative disorder of the central nervous system that mainly affects the motor system. Abnormal accumulation of misfolded alpha-synuclein (aSyn) protein in Lewy bodies contributes to the development of synucleinopathies, including Parkinson's disease (PD) without dementia (PDND), PD with dementia (PDD), and dementia with Lewy bodies (DLBs).

Deleidi M and Maetzler W, in "Protein Clearance Mechanisms of Alpha-Synuclein and Amyloid-Beta in Lewy Body Disorders," International Journal of Alzheimer's Disease, Volume 2012, write, "Protein clearance is critical for the maintenance of the integrity of neuronal cells, and there is accumulating evidence that in most—if not all—neurodegenerative disorders, impaired protein clearance fundamentally contributes to functional and structural alterations eventually leading to clinical symptoms. Dysfunction of protein clearance leads to intra- and extraneuronal accumulation of misfolded proteins and aggregates. The pathological hallmark of Lewy body disorders (LBDs) is the abnormal accumulation of misfolded proteins such as alpha-synuclein (Asyn) and amyloid-beta (Abeta) in a specific subset of neurons, which in turn has been related to deficits in protein clearance" (abstract).

US Patent Application Publication 2014/0324128 to Gross, which is assigned to the assignee of the present application and is incorporated herein by reference, describes apparatus for driving fluid between first and second anatomical sites of a subject. The apparatus comprises (1) a first electrode, configured to be coupled to the first anatomical site of the subject; (2) a second electrode, configured to be coupled to the second anatomical site of the subject; and (3) a control unit, configured to (i) detect a pressure difference between the first and second anatomical sites, and (ii) in response to the detected pressure difference, drive fluid between the first and second anatomical sites by applying a treatment voltage between the first and second electrodes. Other embodiments are also described.

PCT Publication WO 2017/006327 to Gross, which is assigned to the assignee of the present application and is incorporated herein by reference, describes an electrical amyloid beta-clearance system for treating a subject identified as at risk of or suffering from Alzheimer's disease is provided. The system includes (a) midplane treatment electrodes, adapted to be disposed over a superior sagittal sinus, outside and in electrical contact with a skull of a head of the subject; and (b) lateral treatment electrodes, adapted to be disposed between 1 and 12 cm of a sagittal midplane of the skull. The system further includes control circuitry, configured to clear amyloid beta from a subarachnoid space to the superior sagittal sinus, by applying one or more treatment currents between (a) one or more of the midplane treatment electrodes and (b) one or more of the lateral treatment electrodes. Other embodiments are also described.

PCT Publication WO 2017/072769 to Fostick et al., which is assigned to the assignee of the present application and is incorporated herein by reference, describes a system that includes a parenchymal electrode, configured to be implanted in brain parenchyma of a subject identified as at risk of or suffering from a disease; and a cerebrospinal fluid (CSF) electrode, configured to be implanted in a CSF-filled space of a brain of the subject, the CSF-filled space selected from the group consisting of: a ventricular system and a subarachnoid space. Control circuitry is configured to drive the parenchymal electrode and the CSF electrode to clear a substance from the brain parenchyma into the CSF-filled space of the brain. Other embodiments are also described.

SUMMARY OF THE APPLICATION

Some embodiments of the present invention provide techniques for treating or preventing a synucleinopathy, such as Parkinson's disease. In some applications of the present invention, a parenchymal electrode is implanted in parenchyma of the brain, and a cerebrospinal fluid (CSF) electrode is implanted in a CSF-filled space of the brain, e.g., selected from a ventricular system and a subarachnoid space. Control circuitry is activated to drive the parenchymal and the CSF electrodes to clear alpha-synuclein (aSyn) from the brain parenchyma into the CSF-filled space of the brain. Clearance of aSyn may prevent further neuronal death and thus further reduction of dopamine synthesis by dopaminergic neurons. In addition, in some cases, clearance of aSyn may result in increased dopamine synthesis by dopaminergic neurons, as the function of remaining dopaminergic neurons is restored with the reduction in the aSyn burden.

There is therefore provided, in accordance with an application of the present invention, apparatus including:

a parenchymal electrode, configured to be implanted in brain parenchyma of a subject identified as at risk of or suffering from a synucleinopathy;

a cerebrospinal fluid (CSF) electrode, configured to be implanted in a CSF-filled space of a brain of the subject, the CSF-filled space selected from the group consisting of: a ventricular system and a subarachnoid space; and control circuitry, configured to drive the parenchymal and the CSF electrodes to clear alpha-synuclein (aSyn) from the brain parenchyma into the CSF-filled space of the brain.

For some applications, the synucleinopathy is Parkinson's disease, and the parenchymal electrode is configured to be implanted in the subject identified as at risk of or suffering from Parkinson's disease. For some applications, the synucleinopathy is dementia with Lewy bodies (DLBs), and the parenchymal electrode is configured to be implanted in the subject identified as at risk of or suffering from DLBs.

For some applications, the CSF-filled space of the brain is the ventricular system, and the CSF electrode is a ventricular electrode, configured to be implanted in the ventricular system.

For some applications, the ventricular electrode is configured to be implanted in a third ventricle, a fourth ventricle, or a cerebral aqueduct of the ventricular system.

For some applications, the CSF-filled space of the brain is the subarachnoid space, and the CSF electrode is a subarachnoid electrode, configured to be implanted in the subarachnoid space.

For some applications, the control circuitry is configured to configure the parenchymal electrode to be positive, and the CSF electrode to be negative.

For some applications, the control circuitry is configured to configure the parenchymal electrode to be negative, and the CSF electrode to be positive.

For some applications, the control circuitry is configured to additionally apply deep brain stimulation using the parenchymal electrode.

For some applications, the control circuitry is configured to be implanted under skin of the subject.

For some applications, the control circuitry is configured to drive the parenchymal and the CSF electrodes to clear the aSyn by applying a non-excitatory current between the parenchymal and the CSF electrodes.

For some applications, the parenchymal electrode is configured to be implanted in a brainstem of the subject. For some applications, the parenchymal electrode is configured to be implanted such that a substantia nigra of the brainstem is between the parenchymal electrode and a CSF-filled compartment of the ventricular system. For some applications, the CSF electrode is configured to be implanted in the compartment of the ventricular system. For some applications, the parenchymal electrode is configured to be implanted in a midbrain of the brainstem. For some applications, the parenchymal electrode is configured to be implanted in a basal ganglion of the midbrain. For some applications, the parenchymal electrode is configured to be implanted in a substantia nigra of the basal ganglion.

For some applications, the control circuitry is configured to drive the parenchymal and the CSF electrodes to clear the aSyn by applying direct current between the parenchymal and the CSF electrodes. For some applications, the control circuitry is configured to apply the direct current with an average amplitude of between 0.2 and 5 mA. For some applications, the control circuitry is configured to apply the direct current with an average amplitude of less than 1.2 V. For some applications, the control circuitry is configured to apply the direct current as a series of pulses. For some applications, the control circuitry is configured to apply the direct current as the series of pulses having an average pulse duration of between 0.1 ms and 300 seconds. For some applications, the control circuitry is configured to apply the direct current as the series of pulses with a duty cycle of between 1% and 50%.

For some applications, the control unit is configured to:
drive the parenchymal and the CSF electrodes to clear the aSyn by applying a voltage between the parenchymal and the CSF electrodes during each of the pulses,
while applying the voltage, measure a current resulting from application of the voltage during the pulse, and
terminate the pulse upon the measured current falling below a threshold value.

For some applications, the threshold value is based on an initial current magnitude measured upon commencement of the pulse.

For some applications, the apparatus further includes a midplane treatment electrode, adapted to be disposed in or over a superior sagittal sinus, the control circuitry is configured to clear the aSyn from the CSF-filled space of the brain to the superior sagittal sinus, by applying a treatment current between the midplane treatment electrode and the CSF electrode.

For some applications, the midplane treatment electrode is adapted to be disposed over the superior sagittal sinus.

For some applications, the midplane treatment electrode is adapted to be disposed over the superior sagittal sinus, outside and in electrical contact with a skull of a head of the subject.

For some applications, the midplane treatment electrode is adapted to be disposed over the superior sagittal sinus, under a skull of a head of the subject.

For some applications, the midplane treatment electrode is adapted to be implanted in the superior sagittal sinus.

For some applications, the CSF electrode is adapted to be disposed between 1 and 12 cm of a sagittal midplane of a skull of the subject.

For some applications:
the CSF-filled space of the brain is the subarachnoid space,
the CSF electrode is a subarachnoid electrode, configured to be implanted in the subarachnoid space, and
the control circuitry is configured to clear the aSyn from the subarachnoid space to the superior sagittal sinus.

For some applications, the control circuitry is configured to clear the aSyn by electroosmotically driving fluid from the CSF-filled space of the brain to the superior sagittal sinus.

For some applications, the control circuitry is configured to drive the fluid from the CSF-filled space of the brain to the superior sagittal sinus by configuring the midplane treatment electrode to be negative, and the CSF electrode to be positive.

For some applications, the control circuitry is configured to clear the aSyn by electrophoretically driving the aSyn from the CSF-filled space of the brain to the superior sagittal sinus.

For some applications, the control circuitry is configured to apply the treatment current as direct current.

For some applications, the control circuitry is configured to simultaneously drive (a) the parenchymal and the CSF electrodes to clear the aSyn from the brain parenchyma into the CSF-filled space of the brain, and (b) apply the treatment current between the midplane treatment electrode and the CSF electrode to clear the aSyn from the CSF-filled space to the superior sagittal sinus.

For some applications, the control circuitry is configured to apply first, second, and third voltages to the parenchymal electrode, the CSF electrode, and the midplane treatment electrode, respectively, the third voltage more positive than the second voltage, which is in turn more positive than first voltage.

For some applications, the control circuitry is configured to alternatingly (a) drive the parenchymal and the CSF electrodes to clear the aSyn from the brain parenchyma into the CSF-filled space of the brain, and (b) apply the treatment current between the midplane treatment electrode and the CSF electrode to clear the aSyn from the CSF-filled space to the superior sagittal sinus.

For some applications:
the cerebrospinal fluid (CSF) electrode is a first a cerebrospinal fluid (CSF) electrode,
the apparatus further includes:
a midplane treatment electrode, adapted to be disposed in or over a superior sagittal sinus; and
a second cerebrospinal fluid (CSF) electrode, configured to be implanted in a CSF-filled space of a brain of the subject, the CSF-filled space selected from the group consisting of: a ventricular system and a subarachnoid space, and the control circuitry is configured to clear the aSyn from the CSF-filled space of the brain to the superior sagittal sinus, by applying a treatment current between (a) the midplane treatment electrode and (b) the second CSF electrode.

For some applications, the midplane treatment electrode is adapted to be disposed over the superior sagittal sinus.

For some applications, the midplane treatment electrode is adapted to be disposed over the superior sagittal sinus, outside and in electrical contact with a skull of a head of the subject.

For some applications, the midplane treatment electrode is adapted to be disposed over the superior sagittal sinus, under a skull of a head of the subject.

For some applications, the midplane treatment electrode is adapted to be implanted in the superior sagittal sinus.

For some applications, the apparatus further includes:
midplane treatment electrodes, adapted to be disposed over a superior sagittal sinus; and
lateral treatment electrodes, adapted to be disposed between 1 and 12 cm of a sagittal midplane of a skull of a head of the subject, and
the control circuitry is configured to clear the aSyn from the subarachnoid space to the superior sagittal sinus, by applying one or more treatment currents between (a) one or more of the midplane treatment electrodes and (b) one or more of the lateral treatment electrodes.

For some applications, the midplane treatment electrodes are adapted to be disposed over the superior sagittal sinus, outside and in electrical contact with a skull of a head of the subject.

For some applications, the midplane treatment electrodes are adapted to be disposed over the superior sagittal sinus, under a skull of a head of the subject.

For some applications, the control circuitry is configured to clear the aSyn by electroosmotically driving fluid from the subarachnoid space to the superior sagittal sinus.

For some applications, the control circuitry is configured to configure the midplane treatment electrodes to be negative, and the lateral treatment electrodes to be positive.

For some applications:
the lateral treatment electrodes include (a) left lateral treatment electrodes, which are adapted to be disposed left of the sagittal midplane of the skull, and (b) right lateral treatment electrodes, which are adapted to be disposed right of the sagittal midplane of the skull, and
the control circuitry is configured to configure the midplane treatment electrodes to be negative, and the left and the right lateral treatment electrodes to be positive.

For some applications, the control circuitry is configured to clear the aSyn by electrophoretically driving the aSyn from the subarachnoid space to the superior sagittal sinus.

For some applications:
the lateral treatment electrodes include (a) left lateral treatment electrodes, which are adapted to be disposed left of the sagittal midplane of the skull, and (b) right lateral treatment electrodes, which are adapted to be disposed right of the sagittal midplane of the skull, and
the control circuitry is configured to configure the midplane treatment electrodes to be positive, and the left and the right lateral treatment electrodes to be negative.

For some applications, the lateral treatment electrodes are adapted to be implanted under an arachnoid mater of the subject.

For some applications, the lateral treatment electrodes are adapted to be disposed in the subarachnoid space.

For some applications, the lateral treatment electrodes are adapted to be disposed in gray or white matter of a brain of the subject.

For some applications, the control circuitry is configured to apply the one or more treatment currents as direct currents.

There is further provided, in accordance with an application of the present invention, a method including:
implanting a parenchymal electrode in brain parenchyma of a subject identified as at risk of or suffering from a synucleinopathy;
implanting a cerebrospinal fluid (CSF) electrode in a CSF-filled space of a brain of the subject, the CSF-filled space selected from the group consisting of: a ventricular system and a subarachnoid space; and
activating control circuitry to drive the parenchymal and the CSF electrodes to clear alpha-synuclein (aSyn) from the brain parenchyma into the CSF-filled space of the brain.

For some applications, the synucleinopathy is Parkinson's disease, and implanting the parenchymal electrode includes implanting the parenchymal electrode in the subject identified as at risk of or suffering from Parkinson's disease.

For some applications, the synucleinopathy is dementia with Lewy bodies (DLBs), and implanting the parenchymal electrode includes implanting the parenchymal electrode in the subject identified as at risk of or suffering from DLBs.

For some applications:
the CSF-filled space of the brain is the ventricular system,
the CSF electrode is a ventricular electrode,
implanting the CSF electrode including implanting the ventricular electrode in the ventricular system, and
activating the control circuitry includes activating the control circuitry to drive the parenchymal and the ventricular electrodes to clear the aSyn from the brain parenchyma into the ventricular system.

For some applications, implanting the ventricular electrode includes implanting the ventricular electrode in a third ventricle, a fourth ventricle, or a cerebral aqueduct of the ventricular system.

For some applications:
the CSF-filled space of the brain is the subarachnoid space,
the CSF electrode is a subarachnoid electrode,
implanting the CSF electrode includes implanting the subarachnoid electrode in the subarachnoid space, and
activating the control circuitry includes activating the control circuitry to drive the parenchymal and the subarachnoid electrodes to clear the aSyn from the brain parenchyma into the subarachnoid space.

For some applications, implanting the parenchymal electrode includes implanting the parenchymal electrode in a brainstem of the subject. For some applications, implanting the parenchymal electrode includes implanting the parenchymal electrode such that a substantia nigra of the brainstem is between the parenchymal electrode and a CSF-filled compartment of the ventricular system. For some applications, implanting the CSF electrode includes implanting the CSF electrode in the compartment of the ventricular system. For some applications, implanting the parenchymal electrode includes implanting the parenchymal electrode in a midbrain of the brainstem. For some applications, implanting the parenchymal electrode includes implanting the parenchymal electrode in a basal ganglion of the midbrain. For some applications, implanting the parenchymal electrode includes implanting the parenchymal electrode in a substantia nigra of the basal ganglion.

For some applications, activating the control circuitry includes activating the control circuitry to configure the parenchymal electrode to be positive, and the CSF electrode to be negative. For other applications, activating the control circuitry includes activating the control circuitry to configure the parenchymal electrode to be negative, and the CSF electrode to be positive.

For some applications, the method further includes applying deep brain stimulation using the parenchymal electrode.

For some applications, the method further includes implanting the control circuitry under skin of the subject.

For some applications, activating the control circuitry to drive the parenchymal and the CSF electrodes includes activating the control circuitry to drive the parenchymal and the CSF electrodes to clear the aSyn by applying a non-excitatory current between the parenchymal and the CSF electrodes.

For some applications, activating the control circuitry to drive the parenchymal and the CSF electrodes includes activating the control circuitry to drive the parenchymal and the CSF electrodes to clear the aSyn by applying direct current between the parenchymal and the CSF electrodes.

For some applications, activating the control circuitry to apply the direct current includes activating the control circuitry to apply the direct current with an average amplitude of between 0.2 and 5 mA.

For some applications, activating the control circuitry to apply the direct current includes activating the control circuitry to apply the direct current with an average amplitude of less than 1.2 V.

For some applications, activating the control circuitry to apply the direct current includes activating the control circuitry to apply the direct current as a series of pulses.

For some applications, activating the control circuitry to apply the direct current as the series of pulses includes activating the control circuitry to apply the direct current as the series of pulses having an average pulse duration of between 0.1 ms and 300 seconds.

For some applications, activating the control circuitry to apply the direct current as the series of pulses includes activating the control circuitry to apply the direct current as the series of pulses with a duty cycle of between 1% and 50%.

For some applications, activating the control circuitry to drive the parenchymal and the CSF electrodes includes activating the control unit to: drive the parenchymal and the CSF electrodes to clear the aSyn by applying a voltage between the parenchymal and the CSF electrodes during each of the pulses, while applying the voltage, measure a current resulting from application of the voltage during the pulse, and terminate the pulse upon the measured current falling below a threshold value.

For some applications, the threshold value is based on an initial current magnitude measured upon commencement of the pulse.

For some applications, the method further includes disposing a midplane treatment electrode in or over a superior sagittal sinus, and activating the control circuitry includes activating the control circuitry to clear the aSyn from the CSF-filled space of the brain to the superior sagittal sinus, by applying a treatment current between the midplane treatment electrode and the CSF electrode.

For some applications, disposing the midplane treatment electrode includes disposing the midplane treatment electrode over the superior sagittal sinus.

For some applications, disposing the midplane treatment electrode includes disposing the midplane treatment electrode over the superior sagittal sinus, outside and in electrical contact with a skull of a head of the subject.

For some applications, disposing the midplane treatment electrode includes disposing the midplane treatment electrode over the superior sagittal sinus, under a skull of a head of the subject.

For some applications, disposing the midplane treatment electrode includes implanting the midplane treatment electrode in the superior sagittal sinus.

For some applications, implanting the CSF electrode includes implanting the CSF electrode between 1 and 12 cm of a sagittal midplane of a skull of the subject.

For some applications:
the CSF-filled space of the brain is the subarachnoid space,
the CSF electrode is a subarachnoid electrode, and
activating the control circuitry includes activating the control circuitry to clear the aSyn from the subarachnoid space to the superior sagittal sinus.

For some applications, activating the control circuitry includes activating the control circuitry to clear the aSyn by electroosmotically driving fluid from the CSF-filled space of the brain to the superior sagittal sinus.

For some applications, activating the control circuitry includes activating the control circuitry to drive the fluid from the CSF-filled space of the brain to the superior sagittal sinus by configuring the midplane treatment electrode to be negative, and the CSF electrode to be positive.

For some applications, activating the control circuitry includes activating the control circuitry to clear the aSyn by electrophoretically driving the aSyn from the CSF-filled space of the brain to the superior sagittal sinus.

For some applications, activating the control circuitry includes activating the control circuitry to apply the treatment current as direct current.

For some applications, activating the control circuitry includes activating the control circuitry to simultaneously drive (a) the parenchymal and the CSF electrodes to clear the aSyn from the brain parenchyma into the CSF-filled space of the brain, and (b) apply the treatment current between the midplane treatment electrode and the CSF electrode to clear the aSyn from the CSF-filled space to the superior sagittal sinus.

For some applications, activating the control circuitry includes activating the control circuitry to apply first, second, and third voltages to the parenchymal electrode, the CSF electrode, and the midplane treatment electrode, respectively, the third voltage more positive than the second voltage, which is in turn more positive than first voltage.

For some applications, activating the control circuitry includes activating the control circuitry to alternatingly (a) drive the parenchymal and the CSF electrodes to clear the aSyn from the brain parenchyma into the CSF-filled space of the brain, and (b) apply the treatment current between the midplane treatment electrode and the CSF electrode to clear the aSyn from the CSF-filled space to the superior sagittal sinus.

For some applications:
the cerebrospinal fluid (CSF) electrode is a first a cerebrospinal fluid (CSF) electrode,
the method further includes:
disposing a midplane treatment electrode in or over a superior sagittal sinus; and
implanting a second cerebrospinal fluid (CSF) electrode in a CSF-filled space of a brain of the subject, the CSF-filled space selected from the group consisting of: a ventricular system and a subarachnoid space, and activating the control circuitry includes activating the control circuitry to clear the aSyn from the CSF-filled space of the brain to the superior sagittal sinus, by applying a treatment current between (a) the midplane treatment electrode and (b) the second CSF electrode.

For some applications, disposing the midplane treatment electrode includes disposing the midplane treatment electrode over the superior sagittal sinus.

For some applications, disposing the midplane treatment electrode includes disposing the midplane treatment electrode over the superior sagittal sinus, outside and in electrical contact with a skull of a head of the subject.

For some applications, disposing the midplane treatment electrode includes disposing the midplane treatment electrode over the superior sagittal sinus, under a skull of a head of the subject.

For some applications, disposing the midplane treatment electrode includes implanting the midplane treatment electrode in the superior sagittal sinus.

For some applications, the method further includes:
disposing midplane treatment electrodes over a superior sagittal sinus; and
disposing lateral treatment electrodes between 1 and 12 cm of a sagittal midplane of a skull of a head of the subject, and activating the control circuitry includes activating the control circuitry to clear the aSyn from the subarachnoid space to the superior sagittal sinus, by applying one or more treatment currents between (a) one or more of the midplane treatment electrodes and (b) one or more of the lateral treatment electrodes.

For some applications, disposing the midplane treatment electrodes includes disposing the midplane treatment electrodes over the superior sagittal sinus, outside and in electrical contact with a skull of a head of the subject.

For some applications, disposing the midplane treatment electrodes includes disposing the midplane treatment electrodes over the superior sagittal sinus, under a skull of a head of the subject.

For some applications, activating the control circuitry includes activating the control circuitry to clear the aSyn by electroosmotically driving fluid from the subarachnoid space to the superior sagittal sinus.

For some applications, activating the control circuitry includes activating the control circuitry to configure the midplane treatment electrodes to be negative, and the lateral treatment electrodes to be positive.

For some applications:
the lateral treatment electrodes include left lateral treatment electrodes and right lateral treatment electrodes,
disposing the lateral treatment electrodes includes disposing the left lateral treatment electrodes left of the sagittal midplane of the skull, and disposing the right lateral treatment electrodes right of the sagittal midplane of the skull, and
activating the control circuitry includes activating the control circuitry to configure the midplane treatment electrodes to be negative, and the left and the right lateral treatment electrodes to be positive.

For some applications, activating the control circuitry includes activating the control circuitry to clear the aSyn by electrophoretically driving the aSyn from the subarachnoid space to the superior sagittal sinus.

For some applications:
the lateral treatment electrodes include left lateral treatment electrodes and right lateral treatment electrodes,
disposing the lateral treatment electrodes includes disposing the left lateral treatment electrodes left of the sagittal midplane of the skull, and disposing the right lateral treatment electrodes right of the sagittal midplane of the skull, and
activating the control circuitry includes activating the control circuitry to configure the midplane treatment electrodes to be positive, and the left and the right lateral treatment electrodes to be negative.

For some applications, disposing the lateral treatment electrodes includes implanting the lateral treatment electrodes under an arachnoid mater of the subject.

For some applications, disposing the lateral treatment electrodes includes disposing the lateral treatment electrodes in the subarachnoid space.

For some applications, disposing the lateral treatment electrodes includes disposing the lateral treatment electrodes in gray or white matter of a brain of the subject.

For some applications, activating the control circuitry includes activating the control circuitry to apply the one or more treatment currents as direct currents.

The present invention will be more fully understood from the following detailed description of embodiments thereof, taken together with the drawings, in which:

DETAILED DESCRIPTION OF APPLICATIONS

Figure 1A:
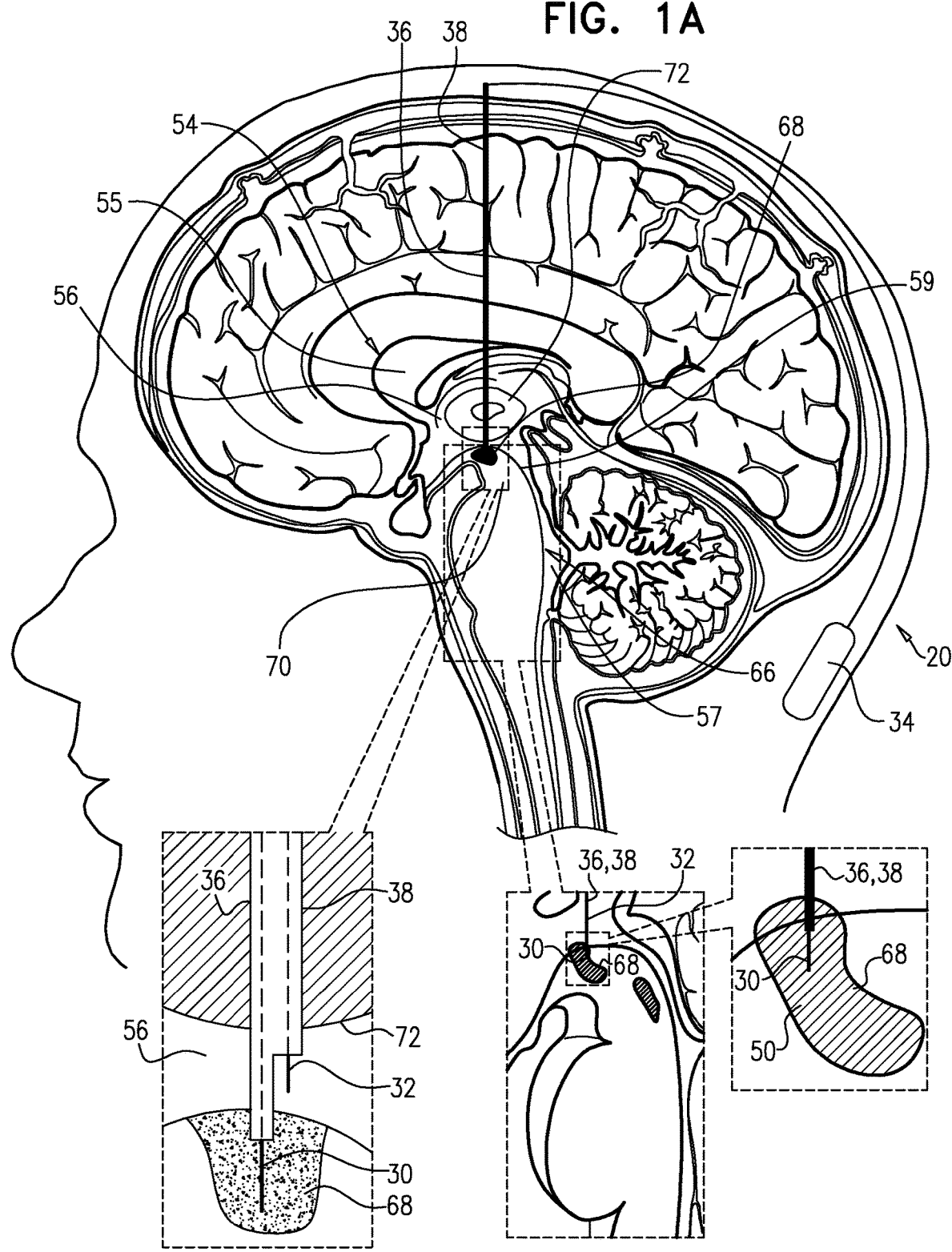
FIGS. 1A-B are schematic illustrations of a system for treating a synucleinopathy, in accordance with respective applications of the present invention.
Figure 1B:
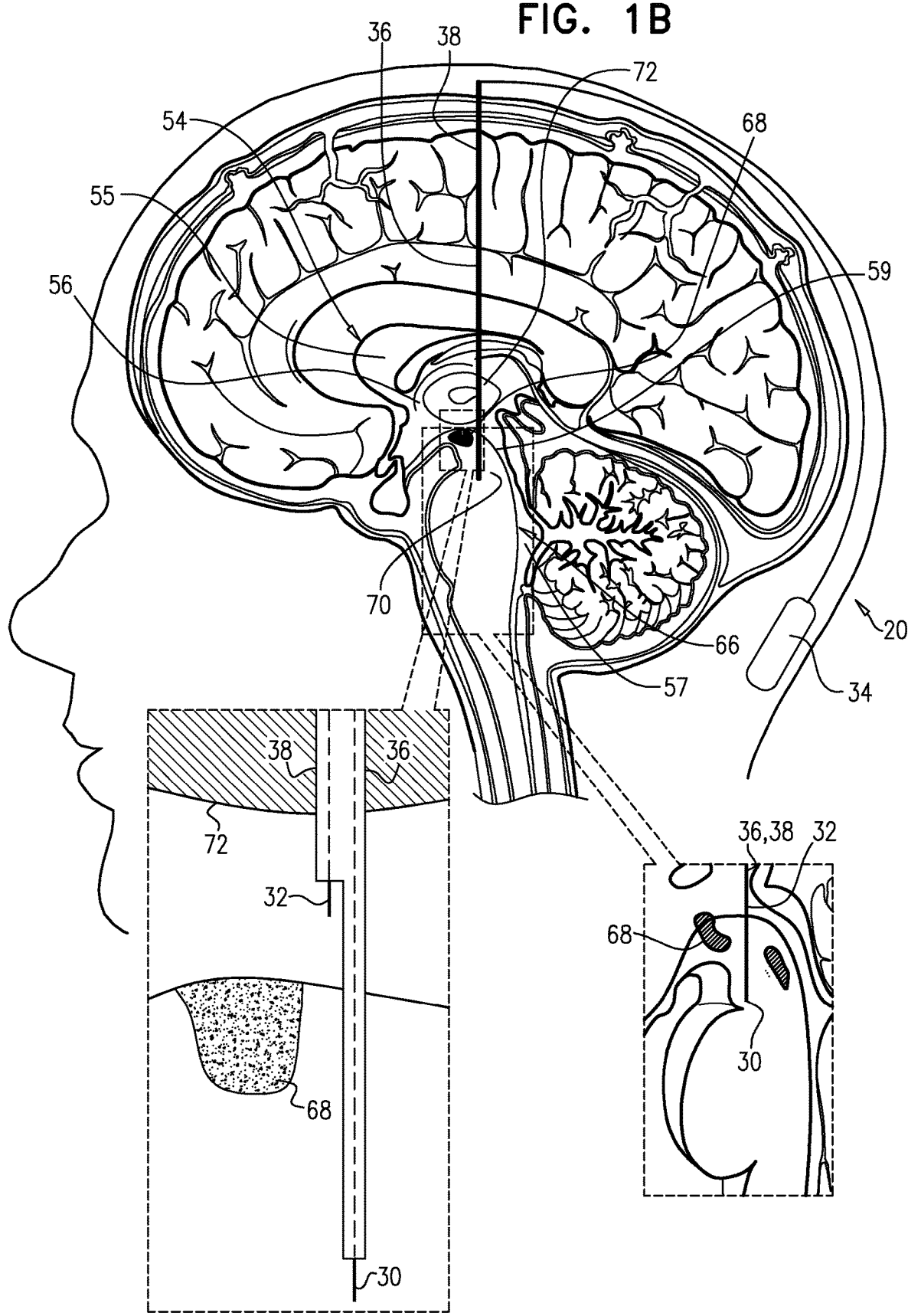

FIGS. 1A-B are schematic illustrations of a system 20 for treating a synucleinopathy, in accordance with respective applications of the present invention. System 20 comprises parenchymal and cerebrospinal fluid (CSF) electrodes 30 and 32, and control circuitry 34, which is electrically coupled to parenchymal and CSF electrodes 30 and 32, typically by parenchymal and CSF electrode leads 36 and 38, respectively, or a combined electrode lead 36/38.

In some applications of the present invention, as shown for parenchymal electrode 30 illustrated in FIGS. 1A-B, parenchymal electrode 30 is implanted in parenchyma 50 of a brain 52 of a subject identified as at risk of or suffering from a synucleinopathy, such as Parkinson's disease (with or without dementia), dementia with Lewy bodies (DLBs), or multiple system atrophy (MSA), e.g., using surgical techniques similar to those used for implantation of electrodes for deep brain stimulation (DBS). CSF electrode 32 is implanted in a CSF-filled space of the brain, such as ventricular system 54 of brain 52 or a subarachnoid space 144 (labeled in FIGS. 2A-G) (e.g., cisterns of subarachnoid space 144). For example, CSF electrode 32 may be implanted using techniques known for implanting hydrocephalus shunts, *mutatis mutandis*. As used in the present application, including in the claims, ventricular system 54 includes and is limited to lateral ventricles 55 (left and right lateral ventricles 55A and 55B, shown in FIGS. 2A-G), a third ventricle 56, a fourth ventricle 57, a cerebral aqueduct 59, an interventricular foramina, a median aperture, and left and right lateral apertures.

Control circuitry 34 is activated to drive parenchymal and CSF electrodes 30 and 32 to clear alpha-synuclein (aSyn) from brain parenchyma 50 into the CSF-filled space, such as ventricular system 54. Typically, the aSyn that is cleared is extracellular aSyn. The aSyn may be cleared through extracellular spaces and the glymphatic system. As used in the present application, including in the claims, clearing aSyn from the brain parenchyma is to be understood as including clearing a portion of the aSyn, without clearing all of the aSyn. Clearance of aSyn may prevent further neuronal death and thus further reduction of dopamine synthesis by dopaminergic neurons. In addition, in some cases, clearance of aSyn may result in increased dopamine synthesis by dopaminergic neurons, as the function of remaining dopaminergic neurons is restored with the reduction in the aSyn burden.

As used in the present application, including the claims, "treating" includes both treating a subject already diagnosed with a synucleinopathy, such as Parkinson's disease, dementia with Lewy bodies (DLBs), or multiple system atrophy (MSA) (such as by delaying, slowing, or reversing progression of the disease, in a patient diagnosed at an early stage), as well as preventing the development of the synucleinopathy in a subject not diagnosed with the disease and/or asymptomatic for the disease. For example, the techniques described herein may be used to prevent or delay the development of the synucleinopathy in responsive to detection of an abnormal level of alpha-synuclein (aSyn), such as using a blood test, a spinal tap, or other biomarkers.

Typically, in order to clear the aSyn from brain parenchyma 50 to outside brain parenchyma 50, control circuitry 34 applies a voltage or a current between parenchymal and CSF electrodes 30 and 32 (e.g., control circuitry 34 regulates the voltage or the current), which typically produces an electric field between (a) parenchymal electrode 30 and (b) CSF electrode 32 and/or the compartment(s) of ventricular system 54 closest to parenchymal electrode 30. For some applications, control circuitry 34 is activated to drive parenchymal and CSF electrodes 30 and 32 to additionally clear amyloid beta from brain parenchyma 50 into the CSF-filled space, which may also treat and/or prevent the synucleinopathy.

Typically, a healthcare worker, such as a physician, activates control circuitry 34 to provide the functions described herein. Activating the control unit may include configuring parameters and/or functions of the control circuitry (such as using a separate programmer or external controller), or activating the control unit to perform functions pre-programmed in the control circuitry. Control circuitry 34 typically comprises appropriate memory, processor(s), and hardware running software that is configured to provide the functionality of control circuitry described herein.

Current may flow generally through tissue that is located between parenchymal and CSF electrodes 30 and 32. Alternatively or additionally, at least a portion of the current may flow between (a) parenchymal electrode 30 and (b) an area of the CSF-filled space (e.g., ventricular system 54) nearest parenchymal electrode 30. The inventors have appreciated that because of the low electrical resistance of cerebrospinal fluid (CSF) in the CSF-filled space, such as ventricular system 54, the ventricles are to some extent a single entity electrically. Therefore, a large portion of the current flows to the nearest portion of ventricular system 54, even if CSF electrode 32 is implanted in a ventricle remote from parenchymal electrode 30.

For some applications, the voltage applied between the electrodes may clear the aSyn electrophoretically, because of a positive or negative charged interface between the surface of the particles of the aSyn and the surrounding brain tissue fluids. For these applications, the voltage applied between the electrodes causes a potential difference between brain parenchyma 50 and the CSF-filled space, such as ventricular system 54, which causes movement of the aSyn from brain parenchyma 50 to the CSF-filled space, such as ventricular system 54. Alternatively or additionally, for some applications, the voltage applied between the electrodes may clear the aSyn electroosmotically, because of a positive or negative charge of fluid in the parenchyma. For these applications, the voltage applied between the electrodes causes a potential difference between brain parenchyma 50 and the CSF-filled space, such as ventricular system 54, which causes increased flow from brain parenchyma 50 to the CSF-filled space, such as ventricular system 54, and thus increased transport of the aSyn from parenchyma 50 to the CSF-filled space, such as ventricular system 54.

For some applications, such as shown in FIGS. 1A-B, system 20 comprises exactly one parenchymal electrode 30 (unlike typical DBS systems). Alternatively or additionally, for some applications, such as shown in FIGS. 1A-B, system 20 comprises exactly one CSF electrode 32. Alternatively, for some applications, system 20 comprises a plurality of parenchymal electrodes 30 and/or a plurality of CSF electrodes 32 (configurations not shown). Parenchymal electrodes 30 may be implanted in one or both hemispheres of brain 52, and/or at one or more than one location in each of the hemispheres. For example, the single CSF electrode 32 may be implanted in one of lateral ventricles 55, third ventricle 56, fourth ventricle 57, or cerebral aqueduct 59, which, as discussed above, are to a large degree in good electrical connectivity with the other ventricles. For other applications (configuration not shown), system 20 comprises (a) exactly two CSF electrodes 32, which are implanted in left and right lateral ventricles 55A and 55B, respectively, or (b) exactly three CSF electrodes 32, which are implanted in left and right lateral ventricles 55A and 55B and third ventricle 56, respectively.

For applications in which system 20 comprises a plurality of parenchymal electrodes 30 and/or a plurality of CSF electrodes 32, system 20 typically comprises a corresponding plurality of parenchymal electrode leads 36 and/or a corresponding plurality of CSF electrode leads 38. Each of the leads may comprise separate electrical insulation, and/or a portion of the leads may be joined and share common electrical insulation. Control circuitry 34 may be activated to independently drive parenchymal electrodes 30, e.g., using separately circuitry. Alternatively, one or more of parenchymal electrodes 30 may be shorted to one another, such that the control circuitry drives the shorted electrodes together. Control circuitry 34 may be activated to drive parenchymal electrodes 30 simultaneously or at different times.

For some applications, such as shown in FIG. 1A, parenchymal electrode 30 is implanted in a substantia nigra 68 of the subject; optionally, two parenchymal electrodes 30 are implanted in both substantiae nigrae 68, respectively (and optionally, two CSF electrodes 32 are implanted in respective compartments of ventricular system 54, such as on opposite sides of brain 52). For example, parenchymal electrode 30 may be implanted at least partially (e.g., entirely) in a pars compacta of substantia nigra 68. Alternatively, for some applications, parenchymal electrode 30 is implanted in a vicinity of (e.g., adjacent) substantia nigra 68, such as a brainstem 66 of the subject, e.g., in a midbrain 70 of brainstem 66, or in a basal ganglion other than substantia nigra 68. Implanting parenchymal electrode 30 in or in a vicinity of (e.g., adjacent) substantia nigra 68 facilitates clearance of aSyn deposits in brain parenchyma 50 of substantia nigra 68. Reducing the concentration of aSyn in substantia nigra 68 is believed by the inventors to treat or prevent synucleinopathies. The reduction in aSyn concentration in parenchyma 50 may reduce the burden of Lewy bodies and/or Lewy neurites in substantia nigra 68.

For some applications, such as shown in FIG. 1B, parenchymal electrode 30 is implanted such that substantia nigra 68 is between parenchymal electrode 30 and a CSF-filled compartment of ventricular system 54. As a result, aSyn deposits are located between parenchymal electrode 30 and the CSF-filled compartment, which enhances the clearance of aSyn caused by the application of current between parenchymal and CSF electrodes 30 and 32. For example, parenchymal electrode 30 may be implanted in a midbrain 70 (as shown) or elsewhere in brainstem 66 (configuration not shown). For some of these applications, CSF electrode 32 is implanted in the compartment of ventricular system 54 in a vicinity of (e.g., adjacent) substantia nigra 68, such as in third ventricle 56, fourth ventricle 57, or cerebral aqueduct 59 of ventricular system 54. Alternatively, CSF electrode 32 is implanted in (a) another compartment of ventricular system 54, such as one of lateral ventricles 55, which, as discussed above, is to a large degree in good electrical connectivity with the other ventricles, or (b) subarachnoid space 144 (which is in fluid communication with ventricular system 54 because CSF drains into cisterns of subarachnoid space 144 via foramina of ventricular system 54).

For some applications, such as shown in FIGS. 1A-B, CSF electrode 32 is implanted in the compartment of ventricular system 54, such as third ventricle 56, fourth ventricle 57, or cerebral aqueduct 59 of ventricular system 54, which are near midbrain 70, brainstem 66, substantia nigra 68, and thalamus 72.

For some applications, control circuitry 34 is activated to drive parenchymal and CSF electrodes 30 and 32 to clear the aSyn by applying a non-excitatory current between parenchymal and CSF electrodes 30 and 32, i.e., the current does not cause propagation of action potentials. Thus, in these applications, control circuitry 34 is activated to set parameters of the current such that the current does not affect, or only minimally affects, neuronal activity. Alternatively, the applied current does excite brain tissue, such as to a small extent.

For some applications, control circuitry 34 is activated to drive parenchymal and CSF electrodes 30 and 32 to clear the aSyn by applying direct current (DC) between parenchymal and CSF electrodes 30 and 32. As used in the present application, including in the claims, direct current means a current having a constant polarity; the amplitude of the direct current may or may not vary over time, and may sometimes be zero.

For some applications, control circuitry 34 is activated to apply the direct current with an average amplitude of at least 0.2 mA (e.g., at least 0.3 mA), no more than 5 mA, and/or between 0.2 mA (e.g., 0.3 mA) and 5 mA. Alternatively or additionally, for some applications, control circuitry 34 is activated to apply the direct current with an average amplitude of less than 1.2 V (such an amplitude may avoid electrolysis in the vicinity of one or both of the electrodes).

For some applications, control circuitry 34 is activated to configure parenchymal electrode 30 to be negative, and CSF electrode 32 to be positive. The inventors believe that extracellular aSyn is generally a negatively-charged molecule. Alternatively, control circuitry 34 is activated to configure parenchymal electrode 30 to be positive, and CSF electrode 32 to be negative.

For some applications, control circuitry 34 is activated to apply the direct current as a series of pulses. For some applications, the series of pulses has an average pulse duration of at least 0.1 ms, no more than 300 seconds, and/or between 0.1 ms and 300 seconds, such as: (a) at least 0.1 ms, no more than 100 ms, and/or between 0.1 and 100 ms, (b) at least 100 ms, no more than 300 seconds (e.g., no more than 500 ms), and/or between 100 and 300 seconds (e.g., between 100 and 500 ms), (c) at least 500 ms, no more than 5 seconds, and/or between 500 ms and 5 seconds, (d) at least 5 seconds, no more than 10 seconds, and/or between 5 and 10 seconds, or (e) at least 10 seconds, no more than 100 seconds, and/or between 10 and 100 seconds. For some applications, the pulses are applied at a frequency of at least 0.001 Hz, no more than 1 kHz, and/or between 0.001 and 1 kHz, such as: (a) at least 100 Hz, no more than 1 kHz, and/or between 100 Hz and 1 kHz, (b) at least 20 Hz, no more than 100 Hz, and/or between 20 and 100 Hz, (c) at least 10 Hz, no more than 90 Hz, and/or between 10 and 90 Hz (e.g., at least 30 Hz, no more than 50 Hz, and/or between 30 Hz and 50 Hz, e.g., 40 Hz) or (d) at least 0.1 Hz (e.g., at least 1 Hz), no more than 10 Hz (e.g., no more than 5 Hz), and/or between 0.1 and 10 Hz, e.g., between 1 and 10 Hz, e.g., between 1 and 5 Hz, such as 2 Hz. Alternatively or additionally, for some applications, the series of pulses has a duty cycle of at least 1%, no more than 50%, and/or between 1% and 50%, such as: (a) at least 1%, no more than 5%, and/or between 1% and 5%, (b) at least 5%, no more than 10%, and/or between 5% and 10%, (c) at least 10%, no more than 25%, and/or between 10% and 25%, or (d) at least 25%, no more than 50%, and/or between 25% and 50%. Typically, but not necessarily, the duty cycle is no more than 90%, because a given level of applied voltage produces higher current in the tissue if the capacitance in the tissue is allowed to discharge between pulses.

For some of the applications in which control circuitry 34 applies a voltage between parenchymal and CSF electrodes 30 and 32 in a series of DC pulses, the resulting current decays because of the effects of tissue electrolytes. The current may decay by about two-thirds of its initial magnitude within tens of milliseconds after commencement of application of each pulse. In order to overcome this capacitance effect, control circuitry 34 is activated to apply the voltage intermittently, in order to provide time periods between pulses during which the capacitance discharges.

For some applications, control circuitry 34 is activated to apply the voltage intermittently with a preprogrammed frequency and/or duty cycle. These parameters may be (a) applicable to all patients or a subgroup of patients, (b) set during a calibration procedure upon implantation of the electrodes, or (c) set based on a geometry of placement of parenchymal and/or CSF electrodes 30 and/or 32. Alternatively, control circuitry 34 is configured to set these parameters in real time by sensing the current resulting from the applied voltage.

For some applications, control circuitry 34 is activated to measure the current resulting from the applied voltage during each of the applied pulses, and to terminate each of the applied pulses when the magnitude of the measured current falls below a threshold value. For example, the threshold value may be a preprogrammed constant, or may be based on (e.g., a percentage of) the initial current magnitude measured upon commencement of the respective pulse. Control circuitry 34 waits during a discharge period before applying the next pulse.

For some applications, control circuitry 34 is activated to apply, between parenchymal and CSF electrodes 30 and 32, alternating current (AC) in:
- a primary subset of the pulses at a primary polarity selected to electrophoretically and/or electroosmotically clear the aSyn, at a primary voltage and with a primary average pulse duration, and
- a secondary subset of the pulses at a secondary polarity opposite the primary polarity, at a secondary voltage less than the primary voltage, and with a secondary average pulse duration greater than the primary average pulse duration.

Because of the lower secondary voltage, the secondary subset of the pulses to a large extent does not reverse the clearance of the aSyn achieved during application of the primary subset of the pulses. This technique may also help avoid electrolysis in the vicinity of one or both of the electrodes, even if the primary voltage is higher than a threshold DC voltage (e.g., 1.2 V) that might otherwise cause electrolysis.

For any of the applications described herein, CSF electrode 32 may be implanted in one of the following sites, rather than in ventricular system 54:
- a central canal of the spinal cord (which is in fluid communication with ventricular system 54); or
- a subarachnoid space 144 (labeled in FIGS. 2A-G) (which is in fluid communication with ventricular system 54 because CSF drains into cisterns of subarachnoid space 144 via foramina of ventricular system 54).

For some applications, instead of implanting CSF electrode 32 in ventricular system 54, an electrode is implanted in superior sagittal sinus 142 (labeled in FIGS. 2A-G).

For any of the applications described herein, parenchymal electrode 30 may be implanted in superior sagittal sinus 142, rather than in brain parenchyma 50 (typically, in these applications, CSF electrode 32 is implanted in ventricular system 54).

Reference is again made to FIGS. 1A-B. For some applications, control circuitry 34 is configured to detect a voltage difference between parenchyma 50 and the CSF-filled space, and set a level of the voltage applied between parenchymal and cerebrospinal fluid (CSF) electrodes 30 and 32 responsively to the detected voltage difference.

Reference is now made to FIGS. 2A-G, which are schematic illustrations of alternative configurations of system 20, in accordance with respective applications of the present invention. These figures show an anterior view of brain 52. In some of these applications, system 20 is configured to, in addition to clearing the aSyn from brain parenchyma 50 into the CSF-filled space, to clear the aSyn from the CSF-filled space (e.g., subarachnoid space 144) to superior sagittal sinus 142. These techniques may be used in combination with any of the techniques described hereinabove. For some of these techniques, control circuitry 34 is configured to apply the treatment current as direct current.

For some applications described with reference to FIGS. 2A-G, control circuitry 34 is configured to simultaneously drive electrodes to both (a) clear the aSyn from brain parenchyma 50 into the CSF-filled space, and (b) clear the aSyn from the CSF-filled space to superior sagittal sinus 142. For example, control circuitry 34 may be configured to apply different respective voltages to parenchymal electrode 30, CSF electrode 32, and a midplane treatment electrode 150, described below. For example, control circuitry 34 may be configured to apply first, second, and third voltages to parenchymal electrode 30, CSF electrode 32, and midplane treatment electrode 150, respectively, the third voltage more positive than the second voltage, which is in turn more positive than first voltage. The total potential difference between the first and the third voltages is typically no greater than 1.2 V volts to avoid electrolysis in the vicinity of one or both of the electrodes.

For other applications described with reference to FIGS. 2A-G, control circuitry 34 is configured to alternatingly drive sets of the electrodes, such as (a) during a plurality of first time periods, driving parenchymal electrode 30 and CSF electrode 32, in order to clear the aSyn from brain parenchyma 50 into the CSF-filled space, and (b) during a plurality of second time periods, typically not overlapping with the first time periods, driving midplane treatment electrode 150 and either CSF electrode 32 or another electrode (described below), in order to clear the aSyn from the CSF-filled space to superior sagittal sinus 142.

For some applications described with reference to FIGS. 2A-G, control circuitry 34 is configured to clear the aSyn to superior sagittal sinus 142 by electroosmotically driving fluid from the CSF-filled space (e.g., subarachnoid space 144) to superior sagittal sinus 142. For some applications, control circuitry 34 is configured to drive the fluid from the CSF-filled space of brain 52 to superior sagittal sinus 142 by configuring midplane treatment electrode 150 to be negative, and CSF electrode 32 to be positive.

For some applications described with reference to FIGS. 2A-G, control circuitry 34 is configured to clear the aSyn by electrophoretically driving the aSyn from the CSF-filled space (e.g., subarachnoid space 144) to superior sagittal sinus 142. For some applications, application of the treatment current causes a potential difference between the CSF-filled space and superior sagittal sinus 142, which causes movement of the aSyn from the CSF-filled space to superior sagittal sinus 142.

Figure 2A:
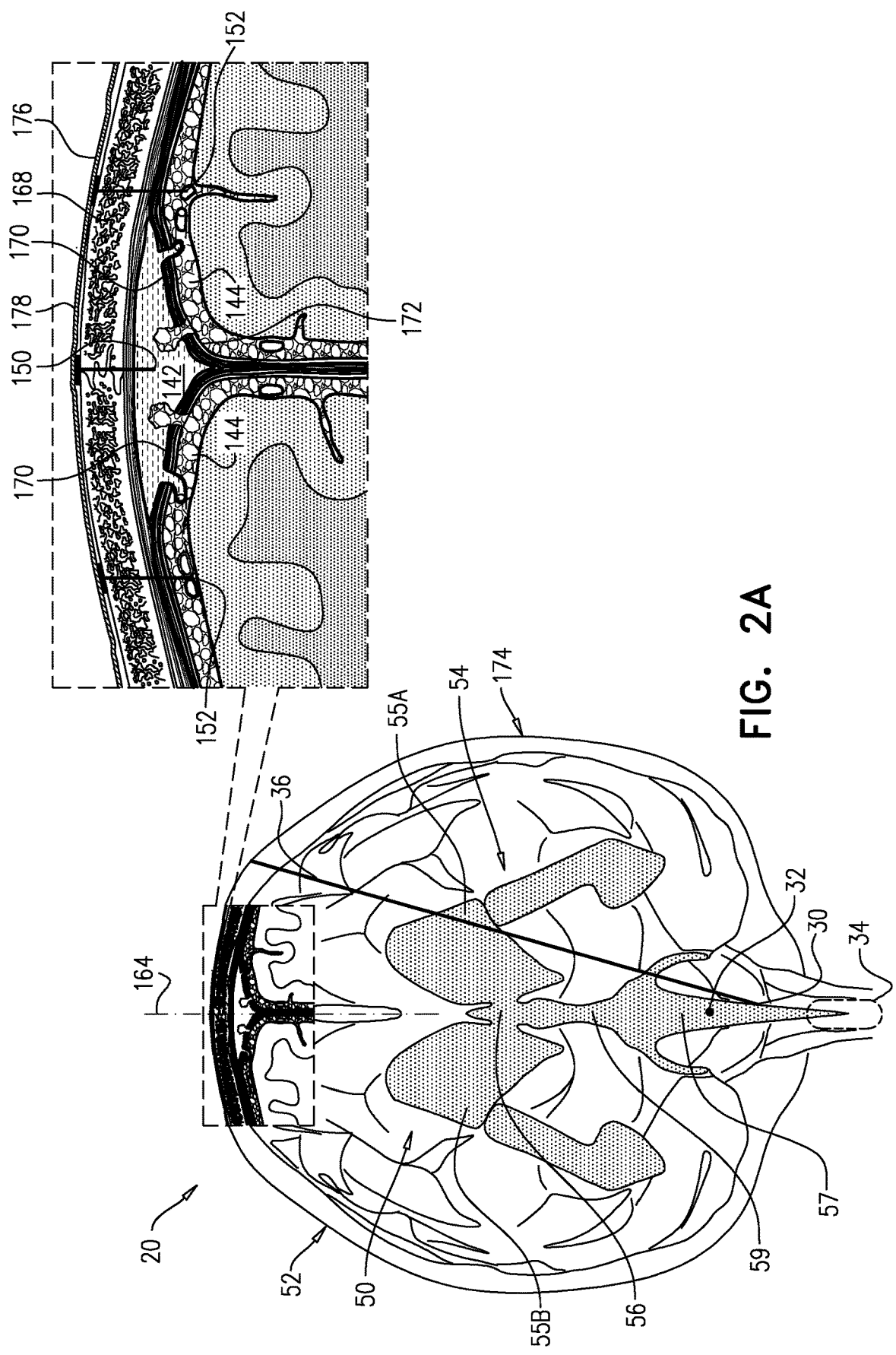
FIGS. 2A-G are schematic illustrations of alternative configurations of the system of FIGS. 1A-B, in accordance with respective applications of the present invention.

For some applications, such as shown in FIG. 2A, parenchymal electrode 30 is implanted in brain parenchyma 50, and CSF electrode 32 is implanted in the CSF-filled space, such as ventricular system 54 or subarachnoid space 144. A midplane treatment electrode 150 is disposed either (a) in superior sagittal sinus 142 (as shown in FIG. 2A), or (b) over superior sagittal sinus 142 (configuration not shown in FIG. 2A, but shown in FIGS. 2B-G). A second CSF electrode 152 is implanted the CSF-filled space, such as ventricular system 54 (configuration not shown in FIG. 2A) or subarachnoid space 144 (as shown in FIG. 2A). Control circuitry 34 is activated to apply (a) a first voltage between parenchymal electrode 30 and CSF electrode 32, to clear the aSyn from brain parenchyma 50 into the CSF-filled space, and (b) a second voltage between midplane treatment electrode 150 and second CSF electrode 152, to clear the aSyn from the CSF-filled space to superior sagittal sinus 142. This technique may be used in combination with the techniques described hereinbelow with reference to FIGS. 2B-G, *mutatis mutandis*.

Figure 2B:
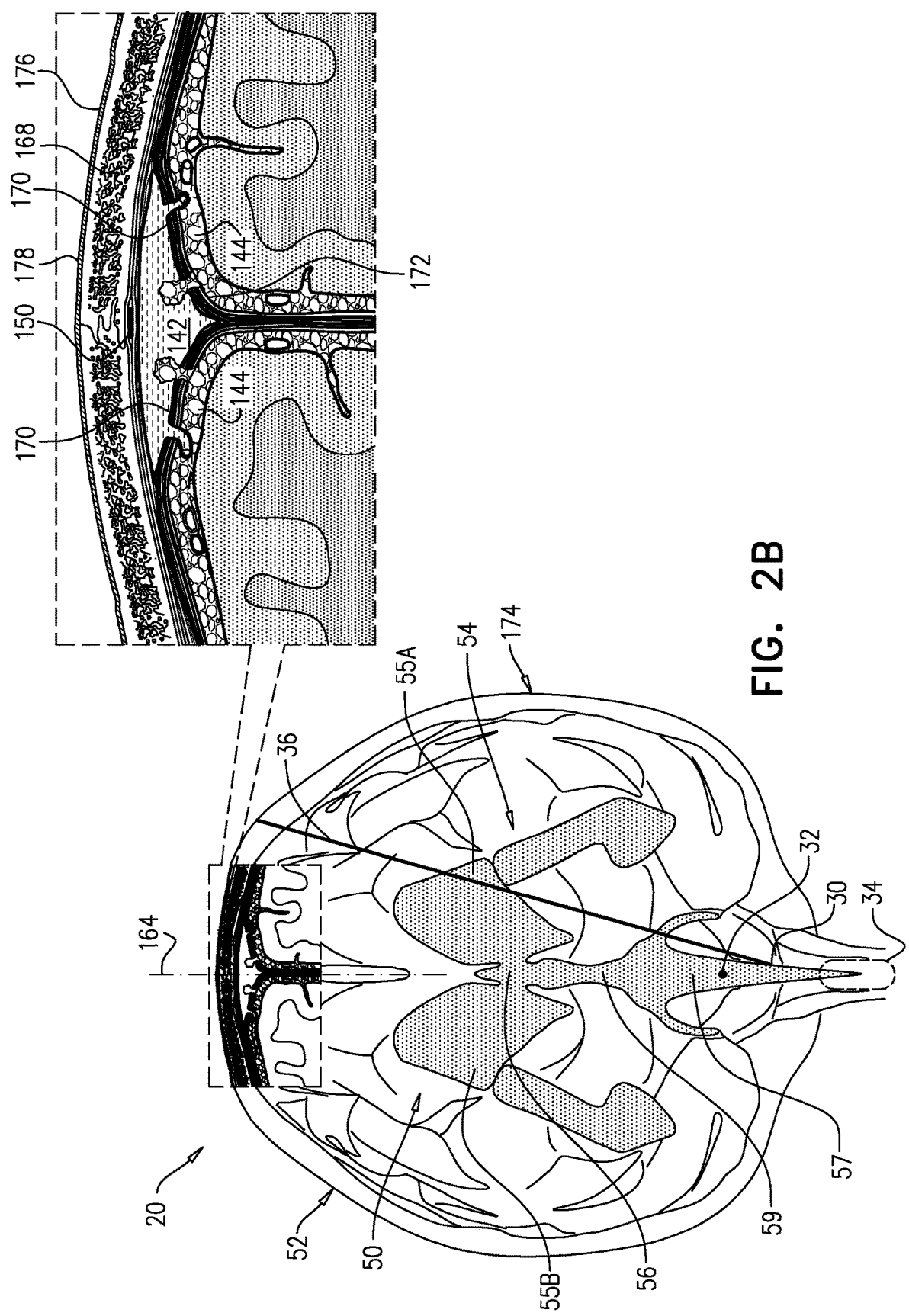

Alternatively, for some applications, such as shown in FIG. 2B, parenchymal electrode 30 is implanted in brain parenchyma 50, and CSF electrode 32 is implanted in the CSF-filled space, such as ventricular system 54 or subarachnoid space 144. Midplane treatment electrode 150 is disposed either (a) in superior sagittal sinus 142 (as shown in FIG. 2A), or (b) over superior sagittal sinus 142 (as shown in FIGS. 2B-G). Control circuitry 34 is activated to apply (a) a first voltage between parenchymal electrode 30 and CSF electrode 32, to clear the aSyn from brain parenchyma 50 into the CSF-filled space, and (b) a second voltage between CSF electrode 32 and midplane treatment electrode 150, to clear the aSyn from the CSF-filled space to superior sagittal sinus 142.

Figure 2C:
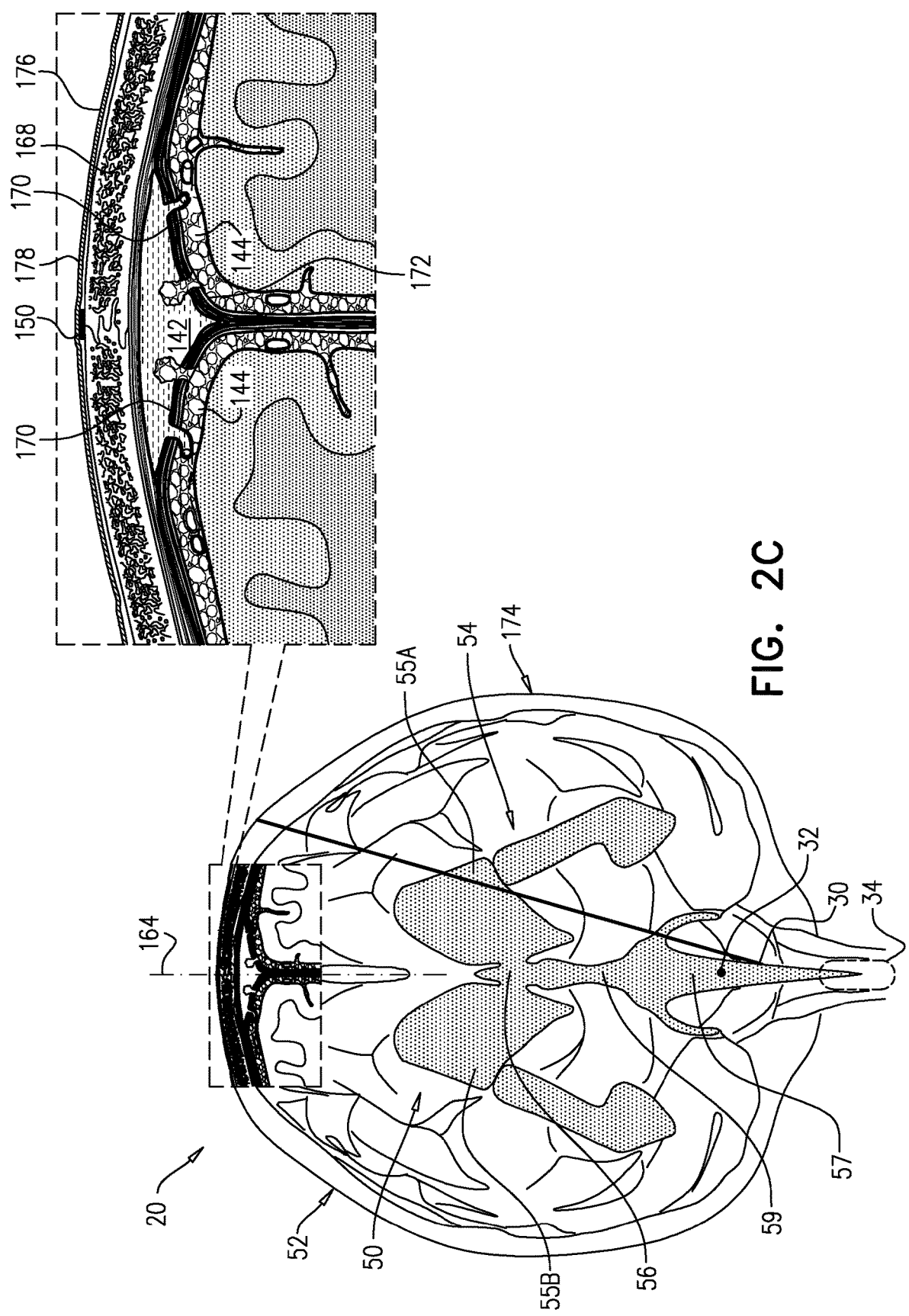

For some applications, such as shown in FIGS. 2B-C, midplane treatment electrode 150 is adapted to be disposed over superior sagittal sinus 142. For some of these applications, midplane treatment electrode 150 is adapted to be disposed under a skull 168 of head 174 of the subject, such as in contact with an outer surface of superior sagittal sinus 142 (either under the dura mater or in contact with an outer surface of the dura mater). For others of these applications, midplane treatment electrode 150 is adapted to be disposed outside and in electrical contact with skull 168. As used in the present application, including in the claims, "over the superior sagittal sinus" means aligned with the superior sagittal sinus at a location more superficial than the superior sagittal sinus, i.e., at a greater distance from a center of the head. In the configurations shown in FIGS. 2B and 2C, control circuitry 34 is configured to clear the aSyn from the CSF-filled space to superior sagittal sinus 142, by applying a treatment current between midplane treatment electrode 150 and CSF electrode 32. Alternatively, the placements of midplane treatment electrode 150 shown in FIGS. 2B and 2C are used in combination with the configuration described hereinabove with reference to FIG. 2A.

Figure 2D:
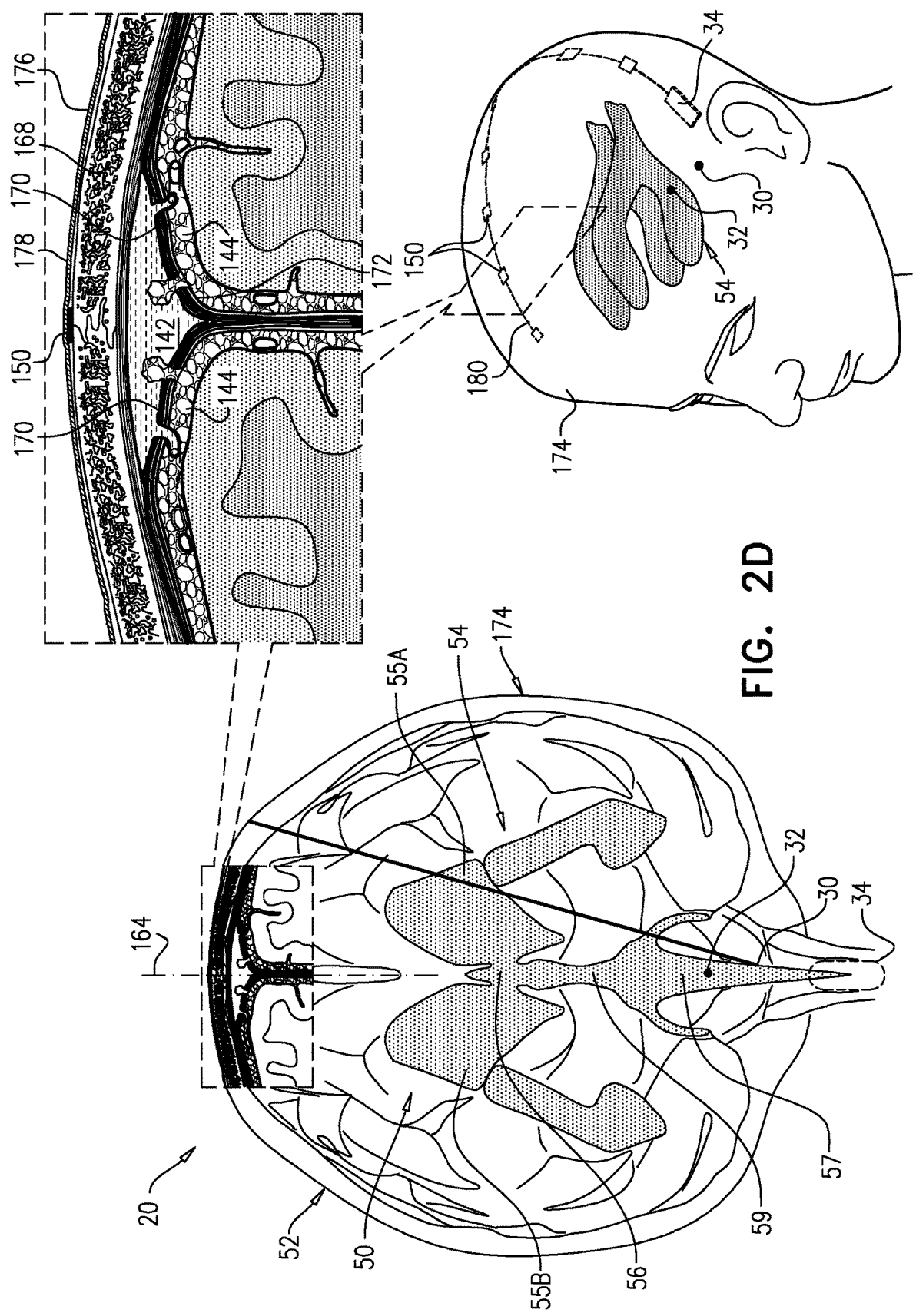

For some applications, such as shown in FIG. 2D, system 20 comprises a plurality of midplane treatment electrodes 150, such as at least 5, no more than 20, and/or between 5 and 20 midplane treatment electrodes 150. Midplane treatment electrodes 150 are disposed either (a) in superior sagittal sinus 142 (configuration not shown in FIG. 2D, but shown in FIG. 2A), or (b) over superior sagittal sinus 142 (as shown in FIG. 2D, or in FIG. 2B).

For any of the applications described herein, including, but not limited to those described with reference to FIGS. 2A-G, CSF electrode 32 may be adapted to be disposed between 1 and 12 cm of a sagittal midplane 164 of skull 168. For some applications, the method may comprise implanting CSF electrode 32 between 1 and 12 cm of sagittal midplane 164 of skull 168.

For any of the applications described herein, including, but not limited to those described with reference to FIGS. 2A-G, the CSF-filled space may be subarachnoid space 144, CSF electrode 32 may be a subarachnoid electrode, configured to be implanted in subarachnoid space 144, and control circuitry 34 may be configured to clear the aSyn from subarachnoid space 144 to superior sagittal sinus 142.

Figure 2E:
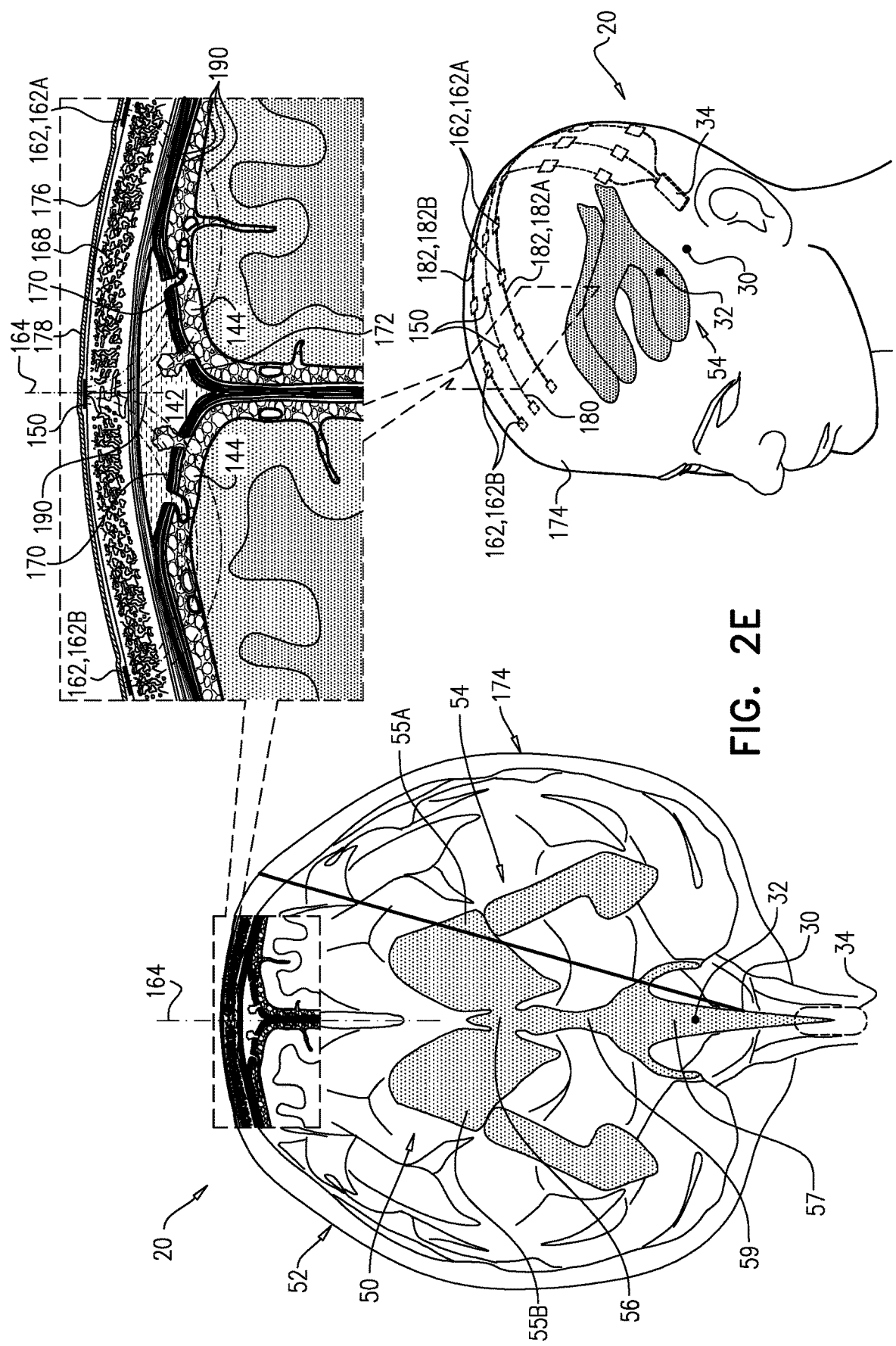
Figure 2F:
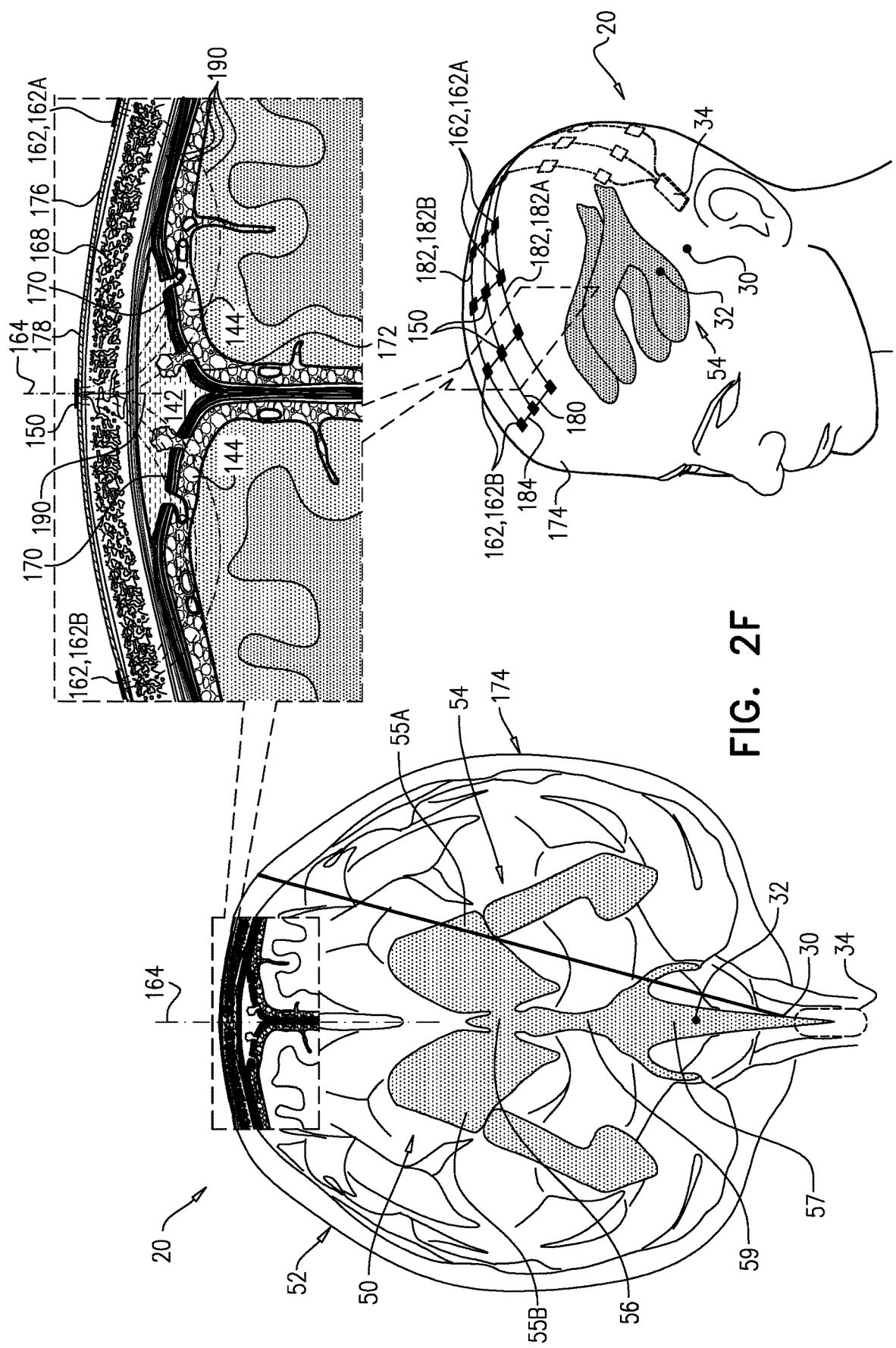
Figure 2G:
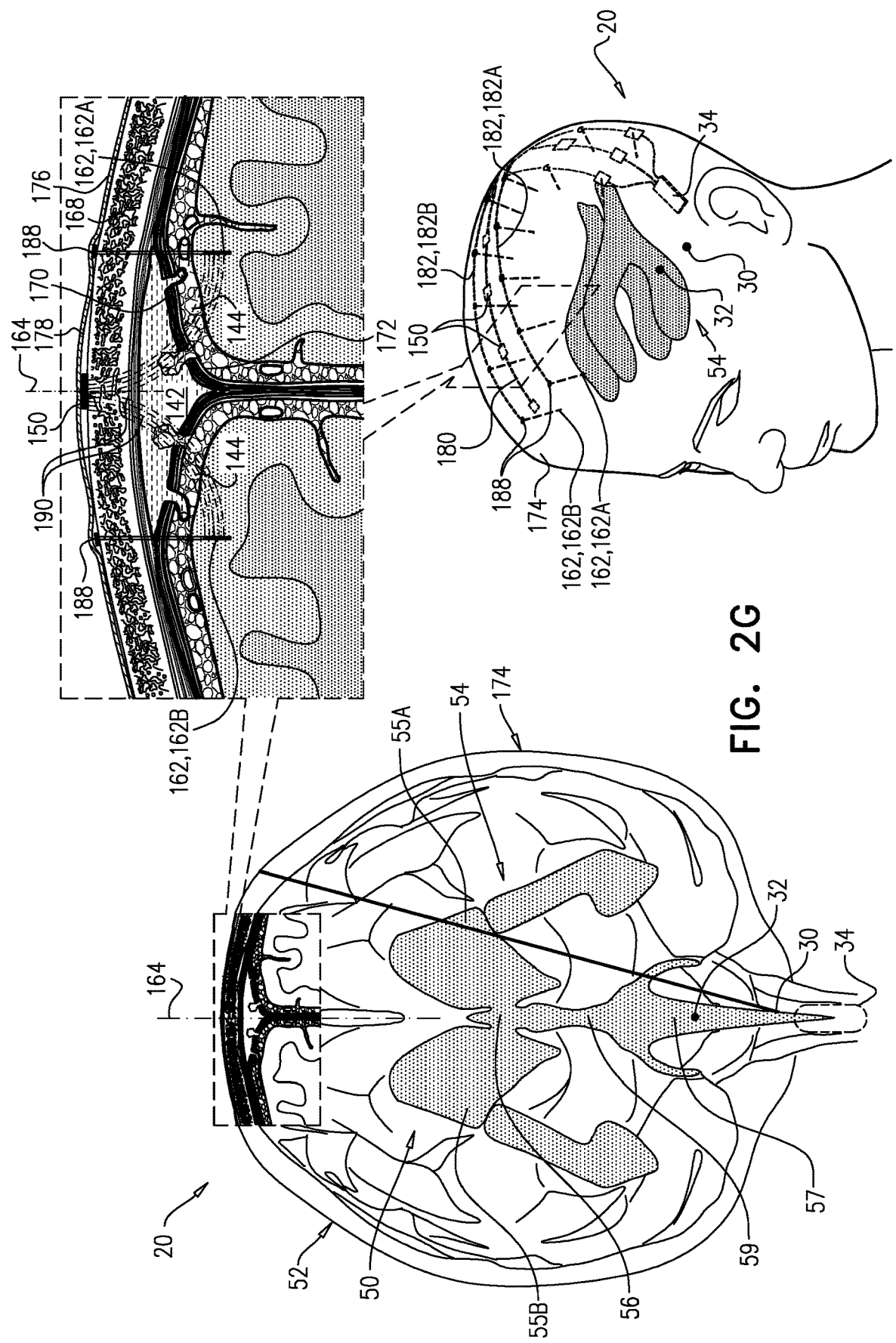

For some applications, such as shown in FIG. 2E-G, system 20 comprises (a) midplane treatment electrodes 150, adapted to be disposed over superior sagittal sinus 142, outside and in electrical contact with skull 168, and (b) lateral treatment electrodes 162, adapted to be disposed at a distance of between 1 and 12 cm of sagittal midplane 164 of skull 168 (the distance is measured in a straight line from a closest portion of each treatment electrode to sagittal midplane 164, rather than along the curvature of skull 168). Control circuitry 34 is configured to clear the aSyn from subarachnoid space 144 to superior sagittal sinus 142, by applying one or more treatment currents between (a) one or more of midplane treatment electrodes 150 and (b) one or more of lateral treatment electrodes 162 (each of the treatment currents is schematically illustrated in the figures by a plurality of current lines 190).

For some applications, system 20 comprises as at least 5, no more than 40, and/or between 5 and 40 lateral treatment electrodes 162, such as between 5 and 20 lateral treatment electrodes 162, or between 10 and 40 lateral treatment electrodes. For some applications, the number of each type of treatment electrode is determined based on the size of head 174 of the subject. For some applications, system 20 comprises twice as many lateral treatment electrodes 162 as midplane treatment electrodes 150.

For some applications, the one or more treatment currents applied using midplane treatment electrodes 150 and lateral treatment electrodes 162 pass between subarachnoid space 144 and superior sagittal sinus 142, via inferolateral surfaces 170 of superior sagittal sinus 142. For some of these applications, at least 40%, e.g., at least 75% or at least 90%, of the treatment currents pass between subarachnoid space 144 and superior sagittal sinus 142, via inferolateral surfaces 170 of superior sagittal sinus 142. For the applications described immediately above, the locations of midplane treatment electrodes 150 and/or lateral treatment electrodes 162 are typically selected such that the one or more treatment currents pass through inferolateral surfaces 170. For example, for configurations in which lateral treatment electrodes 162 are disposed outside and in electrical contact with skull 168, such as described with reference to FIGS. 2C-G, lateral treatment electrodes 162 may be disposed at a distance of at least 4 cm, no more than 12 cm, and/or between 4 and 12 cm of sagittal midplane 164 of skull 168; for configurations in which lateral treatment electrodes 162 are implanted under an arachnoid mater 172 of the subject, such as described with reference to FIGS. 2C-G, lateral treatment electrodes 162 may be disposed at least 1 cm, no more than 3 cm, and/or between 1 and 3 cm of sagittal midplane 164 of skull 168.

For some applications, at least five midplane treatment electrodes 150 are disposed over superior sagittal sinus 142. Alternatively or additionally, for some applications, at least five lateral treatment electrodes 162 between 1 and 12 cm of sagittal midplane 164 of skull 168. For some applications, each of lateral treatment electrodes 162 is disposed between 1 and 12 cm of at least one of midplane treatment electrodes 150.

For some applications, midplane treatment electrodes 150 are disposed within 10 mm of sagittal midplane 164 of skull 168. Alternatively or additionally, for some applications, midplane treatment electrodes 150 are disposed such that at least one of midplane treatment electrodes 150 is at least 5 mm from another one of midplane treatment electrodes 150, no more than 20 mm from another one of midplane treatment electrodes 150, and/or between 5 and 150 mm from another one of midplane treatment electrodes 150. For some applications, at least one of lateral treatment electrodes 162 is disposed is at least 5 mm from another one of lateral treatment electrodes 162.

For some applications, such as shown in FIG. 2E, midplane treatment electrodes 150 are implanted under skin 176 of head 174. For other applications, such as shown in FIG. 2F, midplane treatment electrodes 150 are disposed outside head 174, such as on an external surface 178 of head 174.

For some applications, system 20 further comprises a midplane lead 180, along which midplane treatment electrodes 150 are disposed (e.g., fixed). Midplane lead 180 is disposed outside skull 168 in order to dispose midplane treatment electrodes 150 over superior sagittal sinus 142. For some applications in which midplane treatment electrodes 150 are implanted under skin 176, the implantation is performed by introducing midplane lead 180 through an incision in skin 176, typically at a posterior site of the head, and tunneling the midplane lead toward an anterior site of the head, such as near the forehead. Optionally, each of midplane treatment electrodes 150 is inserted through a respective incision in skin 176, and connected to midplane lead 180.

For some applications, such as shown in FIGS. 2E-F, lateral treatment electrodes 162 are disposed outside and in electrical contact with skull 168. For some of these applications, lateral treatment electrodes 162 are implanted under skin 176 of head 174, such as shown in FIG. 2E. Alternatively, lateral treatment electrodes 162 are disposed outside head 174, such as on external surface 178 of head 174, such as shown in FIG. 2F. For some of these applications, lateral treatment electrodes 162 may be disposed at least 4 cm, no more than 12 cm, and/or between 4 and 12 cm of sagittal midplane 164 of skull 168. (As used in the present application, including in the claims, all specified ranges include their endpoints.) Such positioning may generate one or more treatment currents that pass between subarachnoid space 144 and superior sagittal sinus 142, via inferolateral surfaces 170 of superior sagittal sinus 142, as described above.

For some applications, system 20 further comprises a lateral lead 182, along which lateral treatment electrodes 162 are disposed (e.g., fixed). Lateral lead 182 is disposed outside skull 168, typically within 1 and 12 cm of sagittal midplane 164 of skull 168, in order to dispose lateral treatment electrodes 162. For some applications in which lateral treatment electrodes 162 are implanted under skin 176, the implantation is performed by introducing lateral lead 182 through an incision in skin 176, typically at a posterior site of the head, and tunneling the lateral lead toward an anterior site of the head, such as near the forehead. Optionally, each of lateral treatment electrodes 162 is inserted through a respective incision in skin 176, and connected to lateral lead 182. For some applications, instead of providing lateral lead 182, lateral treatment electrodes 162 are instead coupled to midplane lead 180. Midplane lead 180 is introduced with the lateral electrodes constrained, and, the lateral electrodes are configured upon release to extend laterally, typically automatically. This configuration may also be used for applications in which both left and right lateral electrodes are provided, as described hereinbelow.

For some applications, control circuitry 34 is activated to independently apply the treatment currents between respective pairs of midplane treatment electrodes 150 and lateral treatment electrodes 162. Such independent application of the currents allows continued effective operation of system 20 even if a low resistance should develop between the electrodes of one of the pairs (e.g., because of anatomical variations). For some of these applications, in order to enable such independent application of the currents, midplane lead 180 comprises a plurality of conductive wires corresponding to a number of midplane treatment electrodes 150, and lateral lead 182 comprises a plurality of conductive wires corresponding to a number of lateral treatment electrodes 162. Alternatively, control circuitry 34 and the electrodes implement electrical multiplexing, as is known in the art, in which case each of the leads need only comprise a single conductive wire. Alternatively, for some applications, all of midplane treatment electrodes 150 are electrically coupled to one another (such as by a single conductive wire in the midplane lead), and all of lateral treatment electrodes 162 are electrically coupled to one other (such as by a single conductive wire in the lateral lead).

For some applications of the configuration shown in FIG. 2F, system 20 further comprises one or more thin elongate support elements 184, which couple lateral leads 182 to midplane lead 180, in order to provide proper spacing and alignment between the midplane electrodes and the lateral electrodes. Support elements 184 are typically non-conductive.

For some applications described with reference to FIGS. 2A-G, control circuitry 34 is configured to apply the one or more treatment currents with an average amplitude of between 1 and 3 milliamps. (The resulting voltage is typically greater in the configuration shown in FIGS. 2E-F than in the configuration shown in FIG. 2G, because the one or more treatment currents pass through skull 168 twice.)

For some applications described with reference to FIGS. 2A-G, control circuitry 34 is activated to apply the one or more treatment currents as direct current, typically as a plurality of pulses, for example at greater than 500 Hz and/or less than 2 kHz, e.g., at 1 kHz, or at greater than 0.1 Hz and/or less than 10 Hz, such as between 0.1 and 10 Hz, e.g., greater than 1 Hz and/or less than 5 Hz, e.g., between 1 and 5 Hz. For some applications, a duty cycle of the pulses is above 90%, and for some applications pulses are not used but instead an effective duty cycle of 100% is utilized. Typically, but not necessarily, the duty cycle is 90% or lower, because a given level of applied voltage produces higher current in the tissue if the capacitance in the tissue is allowed to discharge between pulses. For other applications, control circuitry 34 is activated to apply the one or more treatment currents as alternating current with a direct current offset and a constant polarity. For example, the frequency may be at least 0.1 Hz, no more than 100 Hz (e.g., no more than 10 Hz), and/or between 0.1 Hz (e.g., 1 Hz) and 100 Hz (e.g., between 0.1 Hz (e.g., 1 Hz) and 10 Hz).

As mentioned above, for some applications, control circuitry 34 is configured to clear the aSyn by electroosmotically driving fluid from subarachnoid space 144 to superior sagittal sinus 142. For some applications, control circuitry 34 is configured to configure midplane treatment electrodes 150 to be negative, and lateral treatment electrodes 162 to be positive. Alternatively or additionally, increased flow of cerebrospinal fluid (CSF) out of the brain's ventricular system via subarachnoid space 144, as a result of the applied voltage, may itself treat the synucleinopathy, independent of any direct clearance of aSyn in the CSF flow.

For some applications, lateral treatment electrodes 162 comprise (a) left lateral treatment electrodes 162A, which are adapted to be disposed left of sagittal midplane 164 of skull 168, and (b) right lateral treatment electrodes 162B, which are adapted to be disposed right of sagittal midplane 164 of skull 168. For some applications, control circuitry 34 is configured to configure midplane treatment electrodes 150 to be negative, and left and right lateral treatment electrodes 162A and 162B to be positive.

As mentioned above, for some applications, control circuitry 34 is configured to clear the aSyn by electrophoretically driving the aSyn from subarachnoid space 144 to superior sagittal sinus 142. For some applications, lateral treatment electrodes 162 comprise (a) left lateral treatment electrodes 162A, which are adapted to be disposed left of sagittal midplane 164 of skull 168, and (b) right lateral treatment electrodes 162B, which are adapted to be disposed right of sagittal midplane 164 of skull 168. For some of these applications, control circuitry 34 is configured to configure the midplane treatment electrodes 150 to be positive, and left and right lateral treatment electrodes 162A and 162B to be negative. In experiments conducted on behalf of the inventor, amyloid beta was found to be attracted to the positive electrode (anode).

For some applications, lateral treatment electrodes 162 are adapted to be implanted under an arachnoid mater 172 of the subject, such as in brain parenchyma 50 (gray or white matter), as shown in FIG. 2G, or in subarachnoid space 144, such as shown in FIG. 2A. For some applications, the same electrodes serve as both parenchymal electrode 30 and lateral treatment electrodes 162, and are driven by control circuitry 34 either at the same time or at different times. For example, lateral treatment electrodes 162 may comprise needle electrodes, as is known in the art; optionally, lateral treatment electrodes 162 comprise respective proximal anchors 188. This configuration may implement any of the techniques described hereinabove with reference to FIGS. 2A-F, *mutatis mutandis*.

For some of these applications, lateral treatment electrodes 162 are disposed at least 1 cm, no more than 3 cm, and/or between 1 and 3 cm of sagittal midplane 164 of skull 168. Such positioning may generate the treatment currents that pass between subarachnoid space 144 and superior sagittal sinus 142, via inferolateral surfaces 170 of superior sagittal sinus 142, as described above. For some applications, each of lateral treatment electrodes 162 is disposed between 1 and 3 cm of at least one of midplane treatment electrodes 150. For some applications, each of lateral treatment electrodes 162 is disposed between 1 and 3 cm of one of midplane treatment electrodes 150 that is closest to the lateral treatment electrode.

As mentioned above, for some applications, system 20 further comprises midplane lead 180, along which midplane treatment electrodes 150 are disposed (e.g., fixed). Midplane lead 180 is disposed outside skull 168 in order to dispose midplane treatment electrodes 150. For some of these applications, system 20 further comprises (a) a left lateral lead 182A, along which left lateral treatment electrodes 162A are disposed (e.g., fixed), and (b) a right lateral lead 182B, along which right lateral treatment electrodes 162B are disposed (e.g., fixed). Left lateral lead 186A is disposed outside skull 168, typically within 1 and 12 cm of sagittal midplane 164 of skull 168, in order to dispose left lateral treatment electrodes 162A. Right lateral lead 186B is disposed outside skull 168, typically within 1 and 12 cm of sagittal midplane 164 of skull 168, in order to dispose right lateral treatment electrodes 162B.

Reference is again made to 2A-G. For some applications, control circuitry 34 is configured to detect a voltage difference between subarachnoid space 144 and superior sagittal sinus 142, and set a level of the one or more treatment currents responsively to the detected voltage difference.

Although some of the techniques described hereinabove have been described as treating the subject by electroosmotically driving fluid from subarachnoid space 144 to superior sagittal sinus 142, the techniques may alternatively or additionally be used without electroosmosis.

Reference is made to FIGS. 1A-B and 2A-G. For some applications, control circuitry 34 is configured to be implanted subcutaneously, such under skin of the skull of the subject if the housing containing the control circuitry is small, or elsewhere in the subject's body, such as in the upper chest, if the housing of the control circuitry is larger (e.g., includes batteries), with leads through the neck, or optionally in the head. For these applications, control circuitry 34 is typically driven by an external controller that is in wireless or wired communication with control circuitry 34. For some applications, the external controller is mounted on a bed of the subject (e.g., disposed within a mattress), and is configured to activate control circuitry 34 only at night, and/or only when the subject is sleeping. Such nighttime activation may to some degree mimic the natural timing of clearance of the aSyn, during which the extracellular spaces are wider than during wakefulness, which allows more interstitial fluid (ISF) flow within the brain. For other applications, control circuitry 34 is configured to be disposed externally to the subject.

Reference is still made to FIGS. 1A-B and 2A-G. For some applications, parenchymal electrode 30 is further used for applying deep brain stimulation, as is known in the art. For example, the deep brain stimulation may be applied when the electrodes are not being driven to drive the aSyn into the CSF-filled space, such as the ventricular system. As is known in the art, the deep brain stimulation may be applied to reduce tremor and block involuntary movements in patients with motion disorders, such as Parkinson's disease, or to treat epilepsy, cluster headaches, Tourette syndrome, chronic pain, or major depression. The implantation location of parenchymal electrode 30 may be selected to be appropriate for the treatment of a particular condition, as well as for clearing the aSyn.

Reference is still made to FIGS. 1A-B and 2A-G. For some applications, control circuitry 34 is activated to drive the electrodes to drive the aSyn into the CSF-filled space in sessions, each of which has a duration of several seconds or several minutes, or continuously for longer periods (e.g., 30 minutes). For some applications, the electrodes are not driven for a period that is at least an hour. Optionally, control circuitry 34 is activated to drive the electrodes only when the subject is sleeping, such as to take advantage of the widening of extracellular spaces and/or to inhibit any sensations that may be associated with the driving. For example, control circuitry 34 may be activated to use one or more of the electrodes as EEG electrodes to detect sleep. For some applications, power for activating and/or charging control circuitry 34 is transmitted from a wireless energy transmitter in a device applied to the head, such as a hat, or from a wireless energy transmitter in, under, or above a mattress, such as described hereinabove. For some applications, control circuitry 34 is activated to drive the electrodes according to a pre-selected schedule, such as a duty cycle, such as for a few hours per day. For example, control circuitry 34 may be configured to be controlled and/or powered by an extracorporeal control circuitry, such as a control circuitry comprising a wireless transmitter, disposed in and/or in the vicinity of the subject's bed. For some applications, one or more rest periods during which the control circuitry does not drive the electrodes are provided in the pre-selected schedule.

Figure 3A:
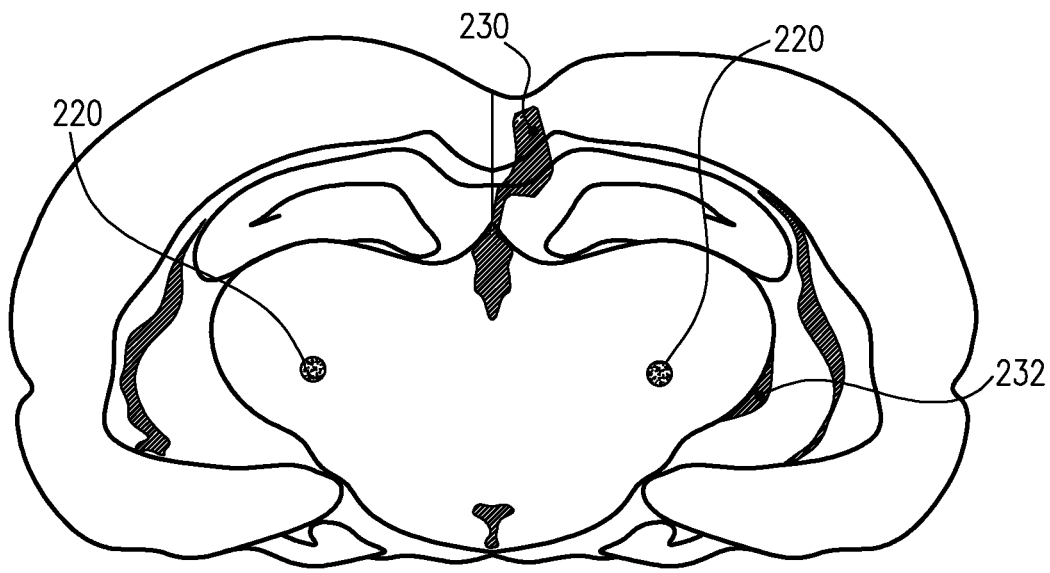
FIGS. 3A-B are schematic illustrations of cross-sections of a rat brain showing results of an animal experiment performed in accordance with an application of the present invention.
Figure 3B:
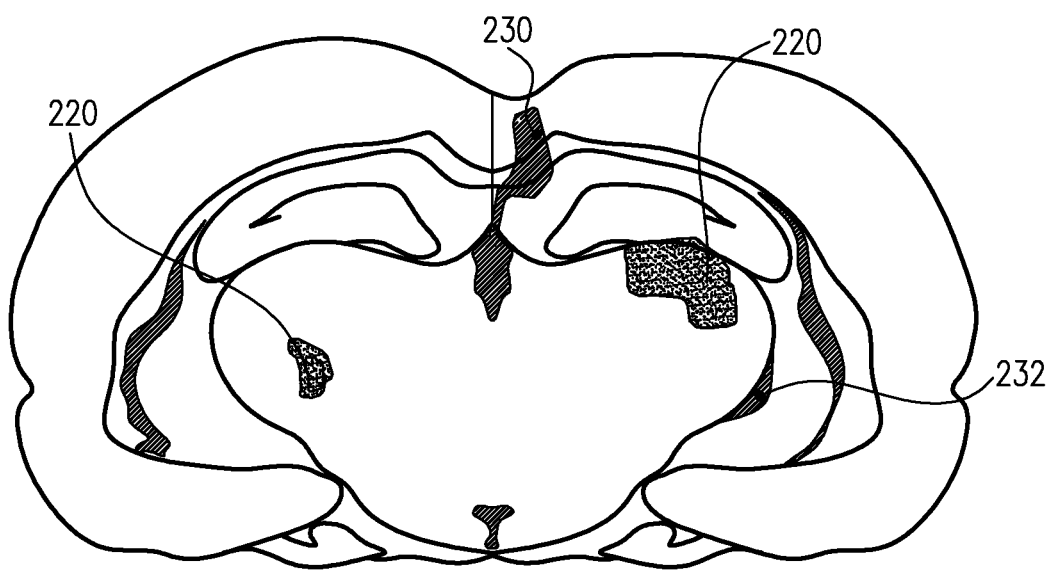

Reference is now made to FIGS. 3A-B, which are schematic illustrations of cross-sections of a rat brain showing results of an animal experiment performed in accordance with an application of the present invention. A rat was anesthetized, a first electrode 230 (a piece of Pt—Ir wire soldered to a miniature connector) was inserted through a hole into the sagittal sinus, and a second electrode 232 (a pieces of Pt—Ir wire soldered to a small electronic connector) was inserted through a hole in dura mater into the right lateral ventricle.

As shown in FIG. 3A, bromephenol blue dye was stereotaxically delivered into both hemispheres of the rat brain at designated coordinates 220 and 222. By using the left hemisphere as a diffusion control, this experimental setup allowed pairwise comparisons within the same animal, thereby ruling out any other effects that might effect a directed migration of the dye in the brain.

Control circuitry was activated to apply a constant-polarity (DC) current to only the right hemisphere, between first and second electrodes 230 and 232, configuring first electrode 230 as a cathode (negative) and second electrode 232 as an anode (positive), because bromephenol blue dye comprises effectively anionic (negatively-charged) molecules. The current was applied by repeatedly alternating between two modes: (a) a first mode, in which the current was applied continuously for 5 minutes at a magnitude of 1-2 mA, and (b) a second mode, in which the current was applied in 10-ms-duration pulses, one pulse per second (i.e., a pulse frequency of 1 Hz), at a magnitude of 1-2 mA.

FIG. 3B shows the displacement of the bromephenol blue dye after application of the current to the right hemisphere. As can be seen, the bromephenol blue dye in the left hemisphere experienced minimal dispersion and no directed displacement. In contrast, in the right hemisphere, the applied current moved the bromephenol blue dye toward the lateral ventricle. The dye moved with the average velocity of 0.28+/−0.006 mm/min, which was more than 14 times greater than the observed diffusion rate in the left hemisphere. In the right hemisphere, the linear displacement of the dye profile center was about 1.9±0.08 mm, while the front of the dye profile reached a maximum distance of about 2.81±0.07 mm from the center of the injection point.

The results of this experiment demonstrated that molecules of dye can be moved within brain tissue by applying a DC current using two electrodes implanted in the brain, and that in such a setup, a natural migration path is toward the ventricles. The inventors believe that application of the current between the electrodes may have moved the dye electrophoretically. The inventors also believe that implantation of the first electrode directly in brain parenchyma, rather than in the superior sagittal sinus, may provide even better current-driven movement of molecules, because the resistance of the parenchyma-sinus interface was calculated as more than two-fold higher than the resistance measured within the parenchyma, based on data collected during the experiment.

Amyloid Beta Mobility and Directionality Assessment

Figure 4:
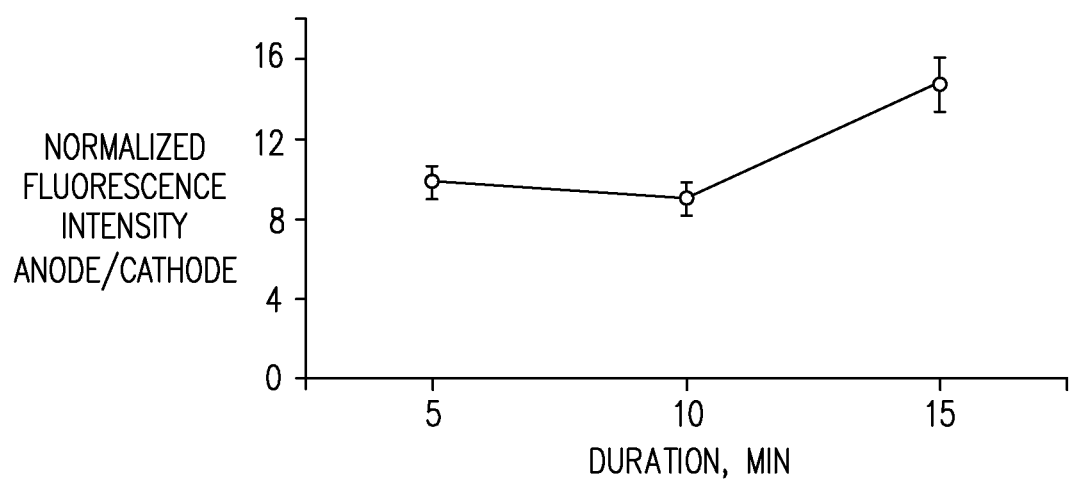
FIG. 4 is a graph showing results of an in vitro experiment performed in accordance with an application of the present invention.

Reference is now made to FIG. 4, which is a graph showing results of an in vitro experiment performed in accordance with an application of the present invention. The inventors believe that aSyn has certain properties that are similar in some respects to amyloid beta, including charge, and thus may be affected in a similar manner by application of the current described herein. The experiment assessed the extent to which application of direct current (DC) eliminated amyloid beta peptides from an artificial cerebrospinal fluid (aCSF) solution (comprising phosphate buffered saline (PBS) solution). Pt—Ir electrodes were inserted into a compartment filled with the aCSF solution. Fluorophore-tagged amyloid beta peptides were dissolved to three different dilution levels (2:500, 5:500, and 10:500). Constant DC currents of three different durations (5, 10, and 15 minutes) were applied from a 1.5 V alkaline battery to the aCSF solution containing the fluorophore-tagged amyloid beta peptides. The directionality and overall capability of amyloid beta to undergo electrophoretic movement was assessed by densitometric analysis of fluorescence on each electrode.

The fluorescence intensity was measured at both electrodes, and the fluorescence intensity was normalized at the positively-charged electrode (anode) with respect to the negatively-charged electrode (cathode) by taking the ratio of fluorescence. Data was averaged from all the measurements and is presented as mean and standard error of mean in FIG. 4.

As can be seen in FIG. 4, current-duration-dependent enhancement of fluorescence was observed near the positively-charged electrode (anode) (for the 2:500 dilution level). The difference in fluorescence between the anodes and the cathodes was statistically significant (one tailed t-test: $p<10^-15$, $t=12.17$) for the current-duration-dependent analysis. The current-duration-dependent trend of fluorescence enhancement on the positively-charged electrode was also statistically significant for 15-minute current application vs. 5- and 10-minute current application (one-way ANOVA: $p<0.001$, $F=8.92$; Holm-Sidak post-hoc analysis: $p<0.01$, $t=3.37$ for 15 minutes vs. 5 minutes and $t=3.889$ for 15 minutes vs. 10 minutes due to nonspecific binding). At all concentrations there was significant attraction of the amyloid beta to the anode vs. the cathode.

These experimental results demonstrate that soluble monomeric amyloid beta in its native conformation is negatively charged in aCSF and is capable of moving in the electrical field without the need to add any amphiphilic detergents to provide the negative charge to the amyloid beta.

Amyloid Beta Electrophoretic Mobility Assessment in Wild Type Mouse Brain Parenchyma An animal experiment was performed in accordance with an application of the present invention. The inventors believe that aSyn has certain properties that are similar in some respects to amyloid beta, including charge, and thus may be affected in a similar manner by application of the current described herein. 20 three-month wild-type mice were anesthetized, and soluble fluorophore-tagged amyloid beta (1-42), HiLyte™ Fluor 488-labeled, Human (AnaSpec, USA) was injected into the brain parenchyma (AP=−2, ML=0.84, DV=1.2). A first Pt—Ir electrode was implanted in brain parenchyma (AP=−2.8, ML=0.84, DV=1.5), and a second Pt—Ir electrode was implanted in the lateral ventricle (AP=−0.5, ML=0.84, DV=1.6). An electrical field generated by the current between the electrodes covered the amyloid beta injection focus. The current application was applied by the repetition of single pulses. The following parameters were used: voltage: 70 V; and frequency: 1 Hz. The current application protocol was as follows: (a) 15 minutes with a pulse duration of 1 ms; (b) 15 minutes with a pulse duration of 10 ms; and (c) 15 minutes with a pulse duration of 100 ms. The frequency was kept constant but the duty cycle was increased.

Assessment of amyloid beta movement directionality in the electrical field was conducted by using antibodies directed against 1-16 amino acid strip of 6E10 (Catalog no. SIG-39320) to visualize the traces of amyloid beta peptide movement in the electrical field. Tissue structure and cell nuclei were visualized by DAPI staining. Amyloid beta movement trajectory was evaluated at different magnifications (4× and 10×). Sagittal slices were stained with antibodies against cell nuclei (blue) and amyloid beta (6E10, green), and imaged by fluorescence microscopy.

Amyloid beta movement was visualized in mouse brains to which the electrical current was applied. The electrode inserted into the lateral ventricle was positively charged, and, similarly to the in vitro experiment described hereinabove with reference to FIG. 4, the applied current was capable of inducing amyloid beta movement.

These experimental results demonstrate that electrophoretic movement of amyloid beta peptides is possible in the brain parenchyma with the electrical current-application protocol used in the experiment. The directionality of amyloid beta peptide movement was similar to that observed the in vitro experiment described hereinabove with reference to FIG. 4.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

US Patent Application Publication 2014/0324128
US Patent Application Publication 2017/0007823
PCT Publication WO 2017/006327
U.S. application Ser. No. 14/926,705, filed Oct. 29, 2015, which issued as U.S. Pat. No. 9,724,515
International Application PCT/IL2016/051161, filed Oct. 27, 2016, which published as PCT Publication WO 2017/072769.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a parenchymal electrode, configured to be implanted in brain parenchyma of a subject identified as at risk of or suffering from a synucleinopathy;
a cerebrospinal fluid (CSF) electrode, configured to be implanted in a CSF-filled space of a brain of the subject, the CSF-filled space selected from the group consisting of: a ventricular system and a subarachnoid space; and
control circuitry, configured to:
drive the parenchymal and the CSF electrodes to clear alpha-synuclein (aSyn) from the brain parenchyma into the CSF-filled space of the brain by applying a non-excitatory current between the parenchymal and the CSF electrodes, and
additionally apply deep brain stimulation using the parenchymal electrode.

2. The apparatus according to claim 1, wherein the synucleinopathy is Parkinson's disease, and wherein the parenchymal electrode is configured to be implanted in the subject identified as at risk of or suffering from Parkinson's disease.

3. The apparatus according to claim 1, wherein the CSF-filled space of the brain is the ventricular system, and wherein the CSF electrode is a ventricular electrode, configured to be implanted in the ventricular system.

4. The apparatus according to claim 1, wherein the CSF-filled space of the brain is the subarachnoid space, and wherein the CSF electrode is a subarachnoid electrode, configured to be implanted in the subarachnoid space.

5. The apparatus according to claim 1, wherein the control circuitry is configured to drive the parenchymal and the CSF electrodes to clear the aSyn by applying non-excitatory direct current between the parenchymal and the CSF electrodes.

6. The apparatus according to claim 5, wherein the control circuitry is configured to apply the non-excitatory direct current with an average amplitude of between 0.2 and 5 mA.

7. The apparatus according to claim 5, wherein the control circuitry is configured to apply the non-excitatory direct current with an average amplitude of less than 1.2 V.

8. The apparatus according to claim 5, wherein the control circuitry is configured to apply the non-excitatory direct current as a series of pulses having an average pulse duration of between 0.1 ms and 300 seconds.

9. A method comprising:
implanting a parenchymal electrode in brain parenchyma of a subject identified as at risk of or suffering from a synucleinopathy;
implanting a cerebrospinal fluid (CSF) electrode in a CSF-filled space of a brain of the subject, the CSF-filled space selected from the group consisting of: a ventricular system and a subarachnoid space; and
activating control circuitry to drive the parenchymal and the CSF electrodes to clear alpha-synuclein (aSyn) from the brain parenchyma into the CSF-filled space of the brain.

10. The method according to claim 9, wherein the synucleinopathy is Parkinson's disease, and wherein implanting the parenchymal electrode comprises implanting the parenchymal electrode in the subject identified as at risk of or suffering from Parkinson's disease.

11. The method according to claim 9,
wherein the CSF-filled space of the brain is the ventricular system,
wherein the CSF electrode is a ventricular electrode,
wherein implanting the CSF electrode comprising implanting the ventricular electrode in the ventricular system, and
wherein activating the control circuitry comprises activating the control circuitry to drive the parenchymal and the ventricular electrodes to clear the aSyn from the brain parenchyma into the ventricular system.

12. The method according to claim 9,
wherein the CSF-filled space of the brain is the subarachnoid space,
wherein the CSF electrode is a subarachnoid electrode,
wherein implanting the CSF electrode comprises implanting the subarachnoid electrode in the subarachnoid space, and
wherein activating the control circuitry comprises activating the control circuitry to drive the parenchymal and the subarachnoid electrodes to clear the aSyn from the brain parenchyma into the subarachnoid space.

13. The method according to claim 9, wherein implanting the parenchymal electrode comprises implanting the parenchymal electrode in a brainstem of the subject.

14. The method according to claim 13, wherein implanting the parenchymal electrode comprises implanting the parenchymal electrode such that a substantia nigra of the brainstem is between the parenchymal electrode and a CSF-filled compartment of the ventricular system.

15. The method according to claim 14, wherein implanting the CSF electrode comprises implanting the CSF electrode in the compartment of the ventricular system.

16. The method according to claim 13, wherein implanting the parenchymal electrode comprises implanting the parenchymal electrode in a midbrain of the brainstem.

17. The method according to claim 16, wherein implanting the parenchymal electrode comprises implanting the parenchymal electrode in a basal ganglion of the midbrain.

18. The method according to claim 17, wherein implanting the parenchymal electrode comprises implanting the parenchymal electrode in a substantia nigra of the basal ganglion.

19. The method according to claim 9, further comprising applying deep brain stimulation using the parenchymal electrode.

20. The method according to claim 9, wherein activating the control circuitry to drive the parenchymal and the CSF electrodes comprises activating the control circuitry to drive the parenchymal and the CSF electrodes to clear the aSyn by applying a non-excitatory current between the parenchymal and the CSF electrodes.

21. The method according to claim 20, wherein activating the control circuitry to drive the parenchymal and the CSF electrodes comprises activating the control circuitry to drive the parenchymal and the CSF electrodes to clear the aSyn by applying direct current between the parenchymal and the CSF electrodes.

22. The method according to claim 21, wherein activating the control circuitry to apply the direct current comprises activating the control circuitry to apply the direct current with an average amplitude of between 0.2 and 5 mA.

23. The method according to claim 21, wherein activating the control circuitry to apply the direct current comprises activating the control circuitry to apply the direct current with an average amplitude of less than 1.2 V.

24. The method according to claim 21, wherein activating the control circuitry to apply the direct current comprises activating the control circuitry to apply the direct current as a series of pulses.

25. The method according to claim 24, wherein activating the control circuitry to apply the direct current as the series of pulses comprises activating the control circuitry to apply the direct current as the series of pulses having an average pulse duration of between 0.1 ms and 300 seconds.

26. The method according to claim 9, further comprising disposing a midplane treatment electrode in or over a superior sagittal sinus, wherein activating the control circuitry comprises activating the control circuitry to clear the aSyn from the CSF-filled space of the brain to the superior sagittal sinus, by applying a treatment current between the midplane treatment electrode and the CSF electrode.

27. The method according to claim 9, wherein the cerebrospinal fluid (CSF) electrode is a first a cerebrospinal fluid (CSF) electrode, wherein the method further comprises:
  disposing a midplane treatment electrode in or over a superior sagittal sinus; and
  implanting a second cerebrospinal fluid (CSF) electrode in a CSF-filled space of a brain of the subject, the CSF-filled space selected from the group consisting of: a ventricular system and a subarachnoid space, and wherein activating the control circuitry comprises activating the control circuitry to clear the aSyn from the CSF-filled space of the brain to the superior sagittal sinus, by applying a treatment current between (a) the midplane treatment electrode and (b) the second CSF electrode.

28. The method according to claim 9, further comprising:
disposing midplane treatment electrodes over a superior sagittal sinus; and
disposing lateral treatment electrodes between 1 and 12 cm of a sagittal midplane of a skull of a head of the subject,
wherein activating the control circuitry comprises activating the control circuitry to clear the aSyn from the subarachnoid space to the superior sagittal sinus, by applying one or more treatment currents between (a) one or more of the midplane treatment electrodes and (b) one or more of the lateral treatment electrodes.

* * * * *